(12) United States Patent
Sheen et al.

(10) Patent No.: US 6,548,743 B1
(45) Date of Patent: Apr. 15, 2003

(54) TRANSGENIC PLANTS EXPRESSING A DUAL-SPECIFICITY MAPK PHOSPHATASE AND USES THEREOF

(75) Inventors: Jen Sheen, Boston, MA (US); Wan-Ling Chiu, Richmond, VA (US)

(73) Assignee: The General Hospital Corporation, Boston, MA (US)

(*) Notice: Subject to any disclaimer, the term of this patent is extended or adjusted under 35 U.S.C. 154(b) by 0 days.

(21) Appl. No.: 09/371,671

(22) Filed: Aug. 10, 1999

Related U.S. Application Data

(60) Provisional application No. 06/115,934, filed on Jan. 14, 1999, and provisional application No. 60/095,938, filed on Aug. 10, 1998.

(51) Int. Cl.[7] .............................. A01H 5/00; A01H 5/10; C12N 5/04; C12N 15/82; C12N 15/54

(52) U.S. Cl. ....................... 800/288; 800/278; 800/287; 800/290; 800/298; 435/419; 435/468; 435/194

(58) Field of Search ................................. 800/278, 287, 800/288, 290, 298; 435/410, 419, 468, 194

(56) References Cited

U.S. PATENT DOCUMENTS

| | | | |
|---|---|---|---|
| 5,527,695 A | 6/1996 | Hodges et al. | |
| 5,658,772 A | 8/1997 | Odell et al. | |
| 5,723,765 A | 3/1998 | Oliver et al. | |

OTHER PUBLICATIONS

Francis, D. and Halford, N. G. "The plant cell cycle." 1995, Physiol. Plant, vol. 93, pp. 365–374.*
Gordon–Dramm, W. J. et al., "Transformation of Maize Cells and Regeneration of Fertile Transgenic Plants." 1990, The Plant Cell, vol. 2, pp. 603–618.*
Datla, R. et al., "Plant promoters for transgene expression." 1997, Biotechnology Annual Review, vol. 3, pp. 269–296.*
Flavell, R. B. et al., "Instability of Transgenes in Plants and Its Implications for Plant Breeding." 1995, International Atomic Energy Agency, pp. 13–22.*
Abel et al., "Transient Transformation of Arabidopsis Leaf Protoplasts: A Versatile Experimental System to Study Gene Expression," *The Plant Journal* 5:421–427 (1994).
Banno et al., "NPK1, a Tobacco Gene that Encodes a Protein with a Domain Homologous to Yeast BCK1, STE11, and Byr2 Protein Kinases," *Mol. Cell. Biol.* 13:4745–4752 (1993).
Banzet et al., "Accumulation of Small Heat Shock Proteins, Including Mitochondrial HSP22, Induced by Oxidative Stress and Adaptive Response in Tomato Cells," *The Plant Journal* 13:519–527 (1998).
Bennett and Tonks, "Regulation of Distinct Stages of Skeletal Muscle Differentiation by Mitogen–Activated Protein Kinases," *Science* 278:1288–1291 (1997).
Bohnert and Jensen, "Strategies for Engineering Water–Stress Tolerance in Plants," *TIBTECH* 14:89–97 (1996).

Bolwell and Wojtaszek, "Mechanisms for the Generation of Reactive Oxygen Species in Plant Defense—A Broad Perspective," *Physiological and Molecular Plant Pathology* 51:347–366 (1997).
Bray, "Plant Responses to Water Deficit," *Trends in Plant Science* 2:48–54 (1997).
Chamnongpol et al., "Defense Activation and Enhanced Pathogen Tolerance Induced by $H_2O_2$ in Transgenic Tobacco," *Proc. Natl. Acad. Sci. USA* 95:5818–5823 (1998).
Cheikh and Jones, "Disruption of Maize Kernel Growth and Development by Heat Stress," *Plant Physiol.* 106:45–51 (1994).
Chen et al., "The Promoter of $H_2O_2$–Inducible, Arabidopsis Glutathione S–Transferase Gene Contains Closely Linked OBF–and OBP1–Binding Sites," *The Plant Journal* 10:955–966 (1996).
Clark et al., "Association of the Arabidopsis CTR1 Raf–Like Kinase with the ETR1 and ERS Ethylene Receptors," *Proc. Natl. Acad. Sci. USA* 95:5401–5406 (1998).
Clarke, "Switching off MAP Kinases," *Current Biology* 4:647–650 (1994).
Damm et al., "Efficient Transformation of *Arabidopsis Thaliana* Using Direct Gene Transfer to Protoplasts," *Mol. Gen. Genet.* 217:6–12 (1989).
Deak et al., "Fas–Induced Proteolytic Activation and Intracellular Redistribution of the Stress–Signaling Kinase MEKK1," *Proc. Natl. Acad. Sci. USA* 95:5595–5600 (1998).
Doi et al., "MSG5, a Novel Protein Phosphatase Promotes Adaptation to Pheromone Response in S. cerevisiae," *The EMBO Journal* 13:61–70 (1994).
Garbers and Simmons, "Approaches to Understanding Auxin Action," *Trends in Cell Biology* 4:245–250 (1994).
Gray et al., "A Role for the Pkc1 MAP Kinase Pathway of *Saccharomyces Cerevisiae* in Bud Emergence and Identification of a Putative Upstream Regulator," *EMBO J.* 16:4924–4937 (1997).

(List continued on next page.)

*Primary Examiner*—David T. Fox
*Assistant Examiner*—Anne Kubelik
(74) *Attorney, Agent, or Firm*—Clark & Elbing, LLP

(57) ABSTRACT

Disclosed are transgenic plants which include a transgene which expresses a phosphatase domain of a dual-specificity mitogen-activated protein kinase (MAPK) phosphatase, wherein the transgene is expressed in the transgenic plant under the control of a promoter that is functional in a plant cell. Also disclosed are methods which are useful for modifying the phenotype of a plant, including the steps of: (a) introducing into a plant cell a transgene comprising DNA encoding a phosphatase domain of a dual-specificity mitogen-activating protein kinase (MAPK) phosphatase operably linked to a promoter functional in plant cells to yield a transformed plant cell; and (b) regenerating a transgenic plant from the transformed cells, wherein the phosphatase domain of the dual-specificity MAPK phosphatase is expressed in the cells of the transgenic plant, thereby modifying the phenotype of the transgenic plant.

24 Claims, 8 Drawing Sheets

OTHER PUBLICATIONS

Green and Fluhr, "UV–B Induced PR–1 Accumulation is Mediated by Active Oxygen Species," *The Plant Cell* 7:203–212 (1995).

Gupta et al., "Identification of a Dual–Specificity Protein Phosphatase that Inactivates a MAP Kinase From Arabidopsis," *The Plant Journal* 16:581–589 (1998).

Gustin et al., "MAP Kinase Pathways in the Yeast *Saccharomyces Cerevisiae*," *Microbiol. Mol. Biol. Rev.* 62:1264–1300 (1998)

Hagen et al., "Auxin–Induced Expression of the Soybean GH3 Promoter in Transgenic Tobacco Plants," *Plant Mol. Biol.* 17:567–579 (1991).

Hardtke et al., "The Arabidopsis Gene Monopteros Encodes a Transcription Factor Mediating Embryo Axis Formation and Vascular Development," *EMBO J.* 17:1405–1411 (1998).

Herskowtiz, "MAP Kinase Pathways in Yeast: For Mating and More," *Cell* 80:187–197 (1995).

Hirt, "Multiple Roles of MAP Kinases in Plant Signal Transduction," *Trends in Plant Science* 2:11–15 (1997).

Holmberg and Bülow, "Improving Stress Tolerance in Plants by Gene Transfer," *Trends in Plant Science* 3:61–66 (1998).

Ichimura et al., "Isolation of ATMEKK1 (A MAP Kinase Kinase)–Interacting Proteins and Analysis of a MAP Kinase Cascade in Arabidopsis," *Biochem. Biophys. Res. Commun.* 253:532–543 (1998).

Inzè and Montagu, "Oxidative Stress in Plants," *Current Opinion in Biotechnology* 6:153–158 (1995).

Ishitani et al., "Genetic Analysis of Osmotic and Cold Stress Signal Transduction in Arabidopsis: Interactions and Convergence of Abscisic Acid–Dependent and Abscisic Acid–Independent Pathways," *The Plant Cell* 9:1935–1949 (1997).

Ishizaki–Nishizawa et al., "Low–Temperature Resistance of Higher Plants is Significantly Enhanced by a Nonspecific Cyanobacterial Desaturase," *Nat. Biotechnol.* 14:1003–1006 (1996).

Jaglo–Ottosen et al., "Arabidopsis CBF1 Overexpression Induces COR Genes and Enhances Freezing Tolerance," *Science* 280:104–106 (1998).

Jonak et al., "MAP Kinases in Plant Signal Transduction," *Cell. Mol. Life Sci.* 55:204–213 (1999).

Karpinski et al., "Systemic Signaling and Acclimation in Response to Excess Excitation Energy in Arabidopsis," *Science* 284:654–657 (1999).

Kato et al., "Bmk1/Erk5 is Required for Cell Proliferation Induced by Epidermal Growth Factor," *Nature* 395:713–716 (1998).

Key, "Modulation of Gene Expression by Auxin," *Bioessays* 11:52–58 (1989).

Kieber et al., "CTR1, A Negative Regulator of the Ethylene Response Pathway in Arabidopsis, Encodes a Member of the Rat Family of Protein Kinases," *Cell* 72:427–441 (1993).

Kishor et al., "Overexpression of $\Delta^1$–Pyrroline–5–Carboxylate Synthetase Increases Proline Production and Confers Osmotolerance in Transgenic Plants," *Plant Physiol* 108:1387–1394 (1995).

Kovtun et al., "Suppression of Auxin Signal Transduction by a MAPK Cascade in Higher Plants," *Nature* 395:716–720 (1998).

Kyriakis and Avruch, "Sounding the Alarm: Protein Kinase Cascades Activated by Stress and Inflammation," *The Journal of Biological Chemistry* 271:24313–24316 (1996).

Lamb and Dixon, "The Oxidative Burst in Plant Disease Resistance," *Annu. Rev. Plant Physiol. Plant Mol. Biol.* 48:251–275 (1997).

Landry et al., Regulation of Actin Dynamics by Stress–Activated Protein Kinase 2 (SAPK2)–Dependent Phosphorylation of Heat–Shock Protein of 27 kDa (Hsp27), *Biochem. Soc. Symp.* 64:79–89 (1999).

Lavoie et al., "Cyclin D1 Expression is Regulated Positively by the p42/p44 $^{MAPK}$ and Negatively by the p38/HOG$^{MAPK}$ Pathway," *J. Biol. Chem.* 271:20608–20616 (1996).

Lee et al., "Derepression of the Activity of Genetically Engineered Heat Shock Factor Causes Constitutive Synthesis of Heat Shock Proteins and Increased Thermotolerance in Transgenic Arabidopsis," *The Plant Journal* 8:603–612 (1995).

Leung et al., "Arabidopsis ABA Response Gene ABI1; Features of a Calcium–Modulated Protein Phosphatase," *Science* 264:1448–1452 (1994).

Leyser, "Auxin Signalling: Protein Stability as a Versatile Control Target," *Curr. Biol.* 8:305–307 (1998).

Liu et al., "Two Transcription Factors, DREB1 and DREB2, with an EREBP/AP2 DNA Binding Domain Separate Two Cellular Signal Transduction Pathways in Drought– and Low–Temperature–Responsive Gene Expression, Respectively, in Arabidopsis," *Plant Cell* 10:1391–1406 (1998).

Liu et al., "Soybean GH3 Promoter Contains Multiple Auxin–Inducible Elements," *Plant Cell* 6:645–657 (1994).

Machida et al., "Progess in Studies of Plant Homologs of Mitogen–Activated Protein (MAP) Kinase and Potential Upstream Components in Kinase Cascades," *Critical Reviews in Plant Sciences* 16:481–496 (1997).

Marrs, "The Functions and Regulation of Glutathione S–Transferases in Plants," *Annu. Rev. Plant Physiol. Plant Mol. Biol.* 47:127–158 (1996).

Michalczuk et al., "Auxin Levels at Different Stages of Carrot Somatic Embryogenesis," *Phytochemistry* 31:1097–1103 (1992).

Misra–Press et al., "A Novel Mitogen–Activated Protein Kinase Phosphatase," *The Journal of Biological Chemistry* 270:14587–14596 (1995).

Mizoguchi et al., "Environmental Stress Response in Plants: The Role of Mitogen–Activated Protein Kinases," *Trends in Biotechnology* 15:15–19 (1997).

Molnar et al., "Cdc42Hs, but Not Rac1, Inhibits Serum–Stimulated Cell Cycle Progression at $G_1$/S Through a Mechanism Requiring p38/RK," *J. Biol. Chem.* 272:13229–13235 (1997).

Mordhorst et al., "Somatic Embryogenesis in *Arabidopsis thaliana* is Facilitated by Mutations in Genes Repressing Meristematic Cell Divisions," *Genetics* 149:549–563 (1998).

Morimoto, "Regulation of the Heat Shock Transcriptional Response: Cross Talk Between a Family of Heat Shock Factors, Molecular Chaperones, and Negative Regulators," *Genes Dev.* 12:3788–3796 (1998).

Morimoto et al., "Stress–Inducible Responses and Heat Shock Proteins: New Pharmacologic Targets for Cytoprotection," *Nat. Biotechnol.* 16:833–838 (1998).

Muda et al., "MKP–3, A Novel Cytosolic Protein–Tyrosine Phosphatase That Exemplifies a New Class of Mitogen–Activated Protein Kinase Phosphatase," *The Journal of Biological Chemistry* 271:4319–4326 (1996).

Muda et al., "Molecular Cloning and Functional Characterization of a Novel Mitogen–Activated Protein Kinase Phosphatase, MKP–4," *The Journal of Biological Chemistry* 272:5141–5151 (1997).

Nakashima et al., "The Expression Pattern of the Gene for NPK1 Protein Kinase Related to Mitogen–Activated Protein Kinase Kinase Kinase (MAPKKK) in a Tobacco Plant: Correlation with Cell Proliferation," *Plant Cell Physiol.* 39:690–700 (1998).

Nishihama et al., "Possible Involvement of Differential Splicing in Regulation of the Activity of Arabidopsis ANP1 that is Related to Mitogen–Activated Protein Kianse Kinase Kinases (MAPKKKs)," *The Plant Journal* 12:39–48 (1997).

Noctor and Foyer, "Ascorbate and Glutathione: Keeping Active Oxygen Under Control," *Annu. Rev. Plant Physiol. Plant Mol. Biol.* 49:249–279 (1998).

Nuccio et al., "Metabolic Engineering of Plants for Osmotic Stress Resistance," *Current Opinion in Plant Biology* 2:128–134 (1999).

Pardo et al., "Stress Signaling Through $Ca^{2+}$/Calmodulin–Dependent Protein Phosphatase Calcineurin Mediates Salt Adaptation in Plants," *Proc. Natl. Acad. Sci. USA* 95:9681–9686 (1998).

Pei et al., "Role of Farnesyltransferase in ABA Regulation of Guard Cell Anion Channels and Plant Water Loss," *Science* 282:287–290 (1998).

Posas et al., "Activation of the Yeast SSK2 MAP Kinase Kinase Kianse by the SSK1 Two–Component Resposne Regulator," *EMBO J.* 17:1385–1394 (1998).

Potts et al., "A Protein–Tyrosine/Serine Phosphatase Encoded by the Genome of the Cyanobacterium *Nostoc commune* UTEX 584," *The Journal of Biological Chemistry* 268:7632–7635 (1993).

Prändl et al., "HSF3, A New Heat Shock Factor from *Arabidopsis thaliana,* Derepresses the Heat Shock Response and Confers Thermotolerance When Overexpressed in Transgenic Plants," *Mol. Gen. Genet.* 258:269–278 (1998).

Prasad, "Mechanisms of Chilling–Induced Oxidative Stress Injury and Tolerance in Developing Maize Seedlings: Changes in Antioxidant System, Oxidation of Proteins and Lipids, and Protease Activities," *The Plant Journal* 10:1017–1026 (1996).

Reichheld et al., "Specific Checkpoints Regulate Plant Cell Cycle Progression in Response to Oxidative Stress," *The Plant Journal* 17:647–656 (1999).

Ribnicky et al., "The Effects of Exogenous Auxins on Endogenous Indole–3–Acetic Acid Metabolism," *Plant Physiol.* 112:549–558 (1996).

Roxas et al., "Overexpression of Glutathione S–Transferase/Glutathione Peroxidase Enhances the Growth of Transgenic Tobacco Seedlings During Stress," *Nature Biotechnology* 15:988–991 (1997).

Saitoh et al., "Mammalian Thioredoxin is a Direct Inhibitor of Apoptosis Signal–Regulating Kinase (ASK) 1," *EMBO J.* 17:2596–2606 (1998).

Schraudner et al., "Ozone–Induced Oxidative Burst in the Ozone Biomonitor Plant, Tobacco Bel W3," *The Plant Journal* 16:235–245 (1998).

Sheen, "Mutational Analysis of Protein Phosphatase 2C Involved in Abscisic Acid Signal Transduction in Higher Plants," *Proc. Natl. Acad. Sci. USA* 95:975–980 (1988).

Sheen, "Protein Phosphatase Activity is Required for Light–Inducible Gene Expression n Maize," *The EMBO Journal* 12:3497–3505 (1993).

Shibuya et al., "TAB1: An Activator of the TAK1 MAPKKK in TGF–β Signal Transduction," *Science* 272:1179–1182 (1996).

Sitbon et al., "Expression of Auxin–Regulated Genes," *Physiological Plantarum* 100:443–455 (1997).

Smith and Walker, "Plant Protein Phosphatases," *Annu. Rev. Plant Physiol. Plant Mol. Biol.* 47:101–125 (1996).

Storozhenko et al., "The Heat–Shock is a Functional Component of the Arabidopsis APX1 Gene Promoter[1]," *Plant Physiol.* 118:1005–1014 (1998).

Sugiura et al., "pmp1+, a Suppressor of Calcineurin Deficiency, Encodes a Novel MAP Kinase Phosphatase in Fission Yeast," *The EMBO Journal* 17:140–148 (1998).

Sun and Tonks, "The Coordinated Action of Protein Tyrosine Phosphatases and Kinases in Cell Signaling," *TIBS* 19:480–485 (1994).

Sun et al., "MKP–1 (3CH134), an Immediate Early Gene Product, is a Dual Specificity Phosphatase That Dephosphorylates MAP Kinase In Vivo," *Cell* 75:487–493 (1993).

Sun et al., "Inhibition of Ras–Induced DNA Synthesis by Expression of the Phosphatase MKP–1," *Science* 266:285–288 (1994).

Takahashi et al., "Characterization of Two Genes Encoding Small Heat–Shock Proteins in *Arabidopsis thaliana,*" *Mol. Gen. Genet.* 219:365–372 (1989).

Takenaka et al., Activation of the Protein Kinase p38 in the Spindle Assembly Checkpoint and Mitotic Arrest, *Science* 280:599–602 (1998).

Tarczynski et al., "Stress Protection of Transgenic Tobacco by Production of the Osmolyte Mannitol," *Science* 259:508–510 (1993).

Tonks and Neel, "From Form to Function: Signaling by Protein Tyrosine Phosphatases," *Cell* 87:365–368 (1996).

Tuomainen et al., "Ozone Induction of Ethylene Emission in Tomato Plants: Regulation by Differential Accumulation of Transcripts for the Biosynthetic Enzymes," *The Plant Journal* 12:1151–1162 (1997).

Ulmasov et al., "The ocs Element in the Soybean GH2/4 Promoter is Activated by Both Active and Inactive Auxin and Salicylic Acid Analogues," *Plant Mol. Biol.* 26:1055–1064 (1994).

Walbot, "Sources and Consequences of Phenotypic and Genotypic Plasticity in Flowering Plants," *Trends in Plant Science* 1:27–32 (1996).

Walker and Estelle, "Molecular Mechanisms of Auxin Action," *Current Opinion in Plant Biology* 1:434–439 (1996).

Ward et al., "Control of MAP Kinase Activation by the Mitogen–Induced Threonine/Tyrosine Phosphatase PAC1," *Nature* 367:651–654 (1994).

Willekens et al., "Catalase is a Sink for $H_2O_2$ and is Indispensable for Stress Defence in $C_3$ Plants," *EMBO J.* 16:4806–4816 (1997).

Wishart and Dixon, "Gathering STYX: Phosphatase–like Form Predicts Functions for Unique Protein–Interaction Domains," *TIBS* 23:301–306 (1998).

Xia et al., JNKK1 Organizes a MAP Kinase Module Through Specific and Sequential Interactions with Upstream and Downstream Components Mediated by its Amino–Terminal Extension, *Genes Dev.* 12:3369–3381 (1998).

Xu et al., "Molecular Characterization of a Tyrosine–Specific Protein Phosphatase Encoded by a Stress–Responsive Gene in Arabidopsis," *Plant Cell* 10:849–857 (1998).

Xu et al., "MEKK1 Phosphorylates MEK1 and MEK2 but Does Not Cause Activation of Mitogen–Activated Protein Kinase," *Proc. Natl. Acad. Sci. USA* 92:6808–6812 (1995).

Yuasa et al., "Tumor Necrosis Factor Signaling to Stress–Activated Protein Kinase (SAPK)/Jun $NH_2$–Terminal Kinase (JNK) and p38," *J. Biol. Chem.* 273:22681–22692 (1998).

Zaitsevskaya–Carter et al., "Spm1, a Stress–Activated MAP Kinase that Regulates Morphogenesis in *S. pombe*," *EMBO J.* 16:1318–1331 (1997).

Zhang et al., "Salicylic Acid Activates a 48–kD MAP Kinase in Tobacco," *Plant Cell* 9:809–824 (1997).

Zhong et al., "Direct Sensing of Heat and Oxidation by Drosophila Heat Shock Transcription Factor," *Mol. Cell* 2:101–108 (1998).

Felix et al., "Rapid Changes of Protein Phosphorylation are Involved in Transduction of the Elicitor Signal in Plant Cells," *Proc. Nat. Acad. Sci. USA* 88:8831–8834 (1991).

Hughes et al., "Complementation of byr1 in Fission Yeast By Mammalian MAP Kinase Kinase Requires Coexpression of Raf Kinase," *Nature* 364:349–352 (1993).

Ito et al., "NPK15, a Tobacco Protein–Serine/Threonine Kinase with a Single Hydrophobic Region Near the Amino–Terminus," *Mol. Gen. Genet.* 245:1–10 (1994).

Seo et al., "Tobacco MAP Kinase: A Possible Mediator in Wound Signal Transduction Pathways," *Science* 270:1988–1992 (1995).

Song et al., "A Receptor Kinase–Like Protein Encoded by the Rice Disease Resistance Gene, Xa21," *Science* 270:1804–1806 (1995).

Watillon et al., "A Calcium/Calmodulin–Binding Serine/Threonine Protein Kinase Homologous to the Mammalian Type II Calcium/Calmodulin–Dependent Protein Kinase Is Expressed in Plant Cells," *Plant Physiology* 101:1381–1384 (1993).

Martin et al., "Map–Based Cloning of a Protein Kinase Gene Conferring Disease Resistance in Tomato," *Science* 262:1432–1436 (1993).

Mizoguchi et al., "A Gene Encoding a Mitogen–Activated Protein Kinase Kinase Kinase is Induced Simultaneously with Genes for a Mitogen–Activated Protein Kinase and an S6 Ribosomal Protein Kinase by Touch, Cold, and Water Stress in *Arabidopsis thaliana*," *Proc. Natl. Acad. Sci USA* 93:765–769 (1996).

Sen Gupta et al., "Increased Resistance to Oxidative Stress in Transgenic Plants that Overexpress Chloroplastic Cu/Zn Superoxide Dismutase," *Proc. Natl Acad. Sci USA* 90:1629–1633 (1993).

Weigel et al., "A developmental Switch Sufficient for Flower Initiation in Diverse Plants," *Nature* 377:495–500 (1995).

Jouannic et al., "Plant MAP Kinase Kinase Kinases Structure, Classification and Evolution," *Gene* 233:1–11 (1999).

\* cited by examiner

```
              M   Y   I       K   E   L   T       E   T   D       E   E   K       R   E   R   S       V   E   D
  1 ATGTATATCA AAGAACTGAC GGAAACGGAT GAGGAGAAGA GGGAGAGATC GGTTGAGGAT

N   V   D       D   G   D   K       A   V   L       V   S   R       G   N   V   I       V   S   T
 61 AACGTNGATG ATGGAGATAA GGCGGTATTG GTGAGCAGAG GAAACGTGAT TGTGTCGACT

T   K   R       A   L   V   G       V   G   A       R   A   L       F   Y   P   T       L   V   Y
121 ACAAAGAGGG CACTCGTTGG TGTTGGTGCT CGTGCTTTGT TTTATCCTAC TCTGGTTTAC

N   V   V       R   N   K   L       E   S   E       F   R   W       W   D   R   V       A   E   F
181 AACGTTGTTA GGAATAAGCT CGAATCTGAG TTTCGCTGGT GGGATCGCGT GGCTGAGTTT

I   L   I       G   A   V   P       F   P   S       D   V   P       Q   L   K   X       L   G   V
241 ATATTACTGG GAGCTGTTCC ATTTCCATCT GATGTTCCAC AGCTGAAAGA NCTCGGTGTT

C   G   V       I   T   L   N       E   P   Y       E   T   L       V   P   S   S       L   Y   K
301 TGTGGAGTGA TCACTCTGAA TGAGCCATAT GAAACTTTGG TTCCATCGTC TCTCTACAAA

S   Y   C       I   D   H   L       V   I   A       T   R   N       Y   C   F   A       P   S   M
361 TCTTACTGCA TTGACCACCT GGTGATTGCT ACAAGAAATT ATTGTTTTGC TCCTTCCATG

E   A   I       C   Q   A   V       E   F   I       H   R   N       A   S   L   G       K   T   T
421 GAAGCAATAT GCCAAGCTGT AGAATTTATC CATAGAAATG CTTCGCTTGG AAAGACGACT

Y   V   H       C   K   A   G       R   G   R       S   T   T       I   F   I   C       Y   L   V
481 TATGTTCACT GCAAAGCGGG TCGGGGTCGC AGCACAACTA TTTTCATATG TTACTTGGTT

Q   H   K       N   M   T   P       E   A   A       Y   S   Y       V   R   S   I       R   P   R
541 CAACACAAAA ACATGACACC TGAAGCAGCA TATTCNTACG TGAGATCAAT CAGGCCCAGG

V   L   L       A   A   A   Q       W   K   A       V   V   E       Y   Y   H   V       K   V   L
601 GTTCTTTTAG CAGCAGCCCA ATGGAAGGCC GTTGTTGAGT ACTACCATGT CAAGGTGCTG

N   T   Q       S   C   L   T       D   A   T       S   A   L       I   P   R   N       V   K   Q
661 AATACTCAGA GTTGCTTAAC TGATGCAACT TCAGCTTTGA TCCCAAGAAA TGTGAAGCAG

V   C   S       G   N   V   V       V   F   D       D   G   S       M   V   V   V       T   H   S
721 GTTTGTTCTG GGAATGTAGT GGTGTTTGAT GATGGGTCAA TGGTTGTAGT CACCCACTCG

D   L   E       G   Y   N   D       D   D   S       R   S   R       R   S   V   K       V   N   G
781 GATCTAGAGG GCTATAATGA TGATGACTCA CGGTCACGGA GGTCAGTGAA AGTTAATGGG

N   E   L       W   A   A   A       D   L   S       M   V   Y       R   V   K   V       V   G
841 AATGAGCTAT GGGCGGCAGC TGCAGATCTG AGTATGGTGT ACAGGGTGAA AGTGGTGGGG

Q   A   A       M   A   R   I       S   C   L       W   L   G       L   R   E   D       Q   K   L
901 CAGGCTGCGA TGGCGAGGAT ATCGTGTCTG TGGCTGGGCT TGCGTGAGGA CCAAAAGCTT

S   G   K       N   L   S   M       G   G   I       S   V   D       I   S   V   Y       *   *
961 TCTGGGAAAA ATCTTTCCAT GGGAGGCATA AGCGTCGACA TTTCTGTCTA CTGATGATGA
1021 TGGCGAAGAA TGAATGCAGG TGAGTCTGCT GGCGAGTGAG TGAATATACC TTATTCACTG
1081 TTTCTCCCCA GTAGAAAAAA AAAGTCTCTA AATAAAAAAA TGGGTCAAAT TAGGTATAGA
```

Fig. 7

```
AtMKP1      iatrdycfapsmealcQAVEEIHRNASLGKTTYVHCKAGRGRSTTIVICYLVQHKNMTPE    60
AtMKP2      vivvdkedtnlemyfdECVDEIDEAKRQGGSVLVHCFVGKSRSVTIVVAYLMKKHGMTLA    60
AtMKP3      iptrdylfapsivditLAVNFIHKNALLGKTTYVHCKAGRGRSTTVVLCYLIEHKSMTVA    60
AtMKP4      ldnekvlqfd------DAIKFLDQCEKDKARVLVHCMSGKSRSPAVVVAYLMKRKGWRLA    54
MKP1-human  ipvednhkadisswfnEAIDFIDSIKNAGGRVFVHCQAGISRSATICLAYLMRTNRVKLD    60
MKP2-human  ipvednhkadisswfmEAIEYIDAVKDCRGRVLVHCQAGISRSATICLAYLMMKKRVRLE    60
MKP3-rat    ipisdhwsqnlsqffpEAISFIDEARGKNCGVLVHCLAGISRSVTVTVAYLMQKLNLSMN    60

AtMKP1      AAYSYVRSIRPRVLLAAAqwkavveyy                                     87
AtMKP2      QALQHVKSKRPVASPNAGFIRQIQDLE                                     87
AtMKP3      AAFEHVRSIRPRVLLHPSqrkvveefs                                     87
AtMKP4      ESHQWVKQRRPSTDISPGkyldfglet                                     87
MKP1-human  EAFEFVKQRRSIISPNFSFMGQLLQFE                                     87
MKP2-human  EAFEFVKQRRSIISPNFSFMGQLLQFE                                     87
MKP3-rat    DAYDIVKMKKSNISPNFNFMGQLLDFE                                     87
```

TRANSGENIC PLANTS EXPRESSING A DUAL-SPECIFICITY MAPK PHOSPHATASE AND USES THEREOF

This application claims benefit of U.S. provisional applications Ser. No. 60/095,938 and No. 60/115,934, filed on Aug. 10, 1998 and Jan. 14, 1999, respectively.

BACKGROUND OF THE INVENTION

This invention relates to the manipulation of plant gene expression and the production of transgenic plants.

Plant growth and development relies on the integration of developmental and environmental signals. In response to these signals, undifferentiated cells at the meristems are able to develop into either vegetative or reproductive structures. The signaling and regulatory mechanisms underlying the maintenance and the differentiation of meristems are mostly unknown. Two plant hormones, auxin and cytokinin, are known to affect meristematic cell division activities. A common phenomenon termed apical dominance results from the suppression of secondary meristems by inhibitory levels of auxin produced at the actively growing apex. Application of cytokinin at the secondary meristems can, however, release this suppression. It is therefore likely that hormones such as auxin and cytokinin are also involved in the maintenance and the regulation of meristem differentiation.

Mitogen-activated protein kinase (MAPK) pathways have been implicated in transmitting hormonal and environmental signals to the cell nucleus in organisms ranging from yeast to humans. For example, in mammals, the primary responses to hormone, growth, and stress signals are mediated by a conserved signaling cascade consisting of three protein kinases, the mitogen-activated protein kinase (MAPK), mitogen-activated protein kinase kinase (MAPKK), and mitogen-activated protein kinase kinase kinase (MAPKKK). MAPKKK phosphorylates and activates MAPKK that, in turn, phosphorylates and activates MAPK. The activated MAPK can be translocated into the nucleus where it phosphorylates transcription factors that control gene expression (Herskowitz, Cell 80: 187–197, 1995; Kyriakis et al., J. Biol. Chem. 271: 24313–24316, 1996). Additionally, in some mammalian cells, the activation of the same MAPK pathway can lead to either cell proliferation or differentiation depending on the duration of the activation. Moreover, dual-specificity MAPK phosphatases have recently been identified as specific regulators which act to turn off and attenuate MAPK signal transduction pathways.

SUMMARY OF THE INVENTION

In one aspect, the invention features a method for modifying a plant phenotype. The method, in general, includes the steps of: (a) introducing into a plant cell a transgene including DNA encoding a phosphatase domain of a dual-specificity mitogen-activating protein kinase (MAPK) phosphatase (or a phosphatase domain thereof) operably linked to a promoter functional in the plant cell to yield a transformed plant cell; and (b) regenerating a transgenic plant from the transformed plant cell, wherein the phosphatase domain of the dual-specificity MAPK phosphatase is expressed in the cells of the transgenic plant, thereby modifying the phenotype of the transgenic plant. In preferred embodiments, the dual-specificity MAPK phosphatase (or a phosphatase domain thereof) hydrolyzes phosphoserine/threonine and phosphotyrosine residues on a protein substrate. In other preferred embodiments, the dual-specificity MAPK phosphatase (or a phosphatase domain thereof) is a eukaryotic dual-specificity MAPK phosphatase (e.g., an approximately full-length MKP-1 or a polypeptide including approximately amino acids 1–314 of MKP-1). In particular applications, the method is useful for modifying a plant's phenotype for the production of plants having increased yield; increased flower production; early flowering; increased reproductive capacity; decreased vegetative growth; delayed senescence; decreased sensitivity to auxin; increased seed production; or increased regeneration capacity in vitro.

In related aspects, the invention features a plant (or plant cell, plant tissue, plant organ, or plant part) including a transgene capable of expressing a phosphatase domain of a dual-specificity MAPK phosphatase, wherein the transgene is expressed in the transgenic plant under the control of a promoter that is functional in a plant cell. In preferred embodiments, the dual-specificity MAPK phosphatase hydrolyzes phosphoserine/threonine and phosphotyrosine residues on a protein substrate. In other preferred embodiments, the dual-specificity MAPK phosphatase is a eukaryotic dual-specificity MAPK phosphatase (e.g., an approximately full-length MKP-1 or a polypeptide including approximately amino acids 1–314 of MKP-1).

In related aspects, the invention also features seeds and cells from a plant which includes a transgene capable of expressing a phosphatase domain of a dual-specificity MAPK phosphatase (or a phosphatase domain thereof).

In general, the phosphatase domain used in the methods or transgenic plants of the invention is generally expressed by itself, as a dual-specificity MAPK phosphatase polypeptide or phosphatase domain-containing fragment thereof, or as part of a genetically engineered chimeric polypeptide. Useful dual-specificity MAPK phosphatases include those that inactivate a MAPK pathway cascade; improve yields; increase flower production; promote early flowering; increase reproductive season; decrease vegetative growth; delay senescence; decrease sensitivity to auxin; increase seed production; or increase plant regeneration in vitro. Exemplary phosphatase domains include, without limitation, those that are substantially identical or identical to the phosphatase domains of MKP-1, MKP-2, MKP-3, MKP-4, PAC-1, MSG5, Pmp1, IphP, AtMKP1, AtMKP2, AtMKP3, or AtMKP3. Preferably, the methods and plants of the invention specifically utilize the phosphatase domain of MKP-1 or amino acids 1–314 of MKP-1. In other preferred embodiments, a full-length dual-specificity MAPK phosphatase polypeptide or a phosphatase domain containing fragment thereof that is substantially identical or identical to MKP-1, MKP-2, MKP-3, MKP-4, PAC-1, MSG5, Pmp1, IphP, AtMKP-1, AtMKP-2, AtMKP-3, or AtMKP-4 is utilized.

The DNA encoding the dual-specificity MAPK phosphatase polypeptide or phosphatase domain-containing fragment thereof is, in general, constitutively expressed in the transgenic plant. However, if desired, the domain may be inducibly expressed, or such a domain may be expressed in a cell-specific, tissue-specific, or organ-specific manner.

In other preferred embodiments, the invention features an isolated nucleic acid molecule including a sequence encoding a dual-specificity MAPK phosphatase having at least 40% identity with the amino acid sequence shown in FIG. 7 (SEQ ID NO: 2). In preferred embodiments, the sequence that encodes a dual-specificity MAPK phosphatase includes the amino acid sequence shown in FIG. 7 (SEQ ID NO: 2). Preferred nucleic acid molecules are obtained from cruciferous plants, for example, Arabidopsis thaliana. An exemplary nucleic acid molecule of a cruciferous dual-specificity MAPK phosphatase is shown in FIG. 7 (SEQ ID NO: 1).

In still another aspect, the invention features a plant including an isolated nucleic acid molecule including a sequence (encoding a dual-specificity MAPK phosphatase having at least 40% identity with the amino acid sequence shown in FIG. 7 (SEQ ID NO: 2). In addition, the invention features seeds and cells from such plants, as well as parts of such plants. These plants may be produced according to conventional methods of molecular biology using any crop or ornamental plant, e.g., those plants described herein.

In yet another aspect, the invention features a substantially pure dual-specificity MAPK phosphatase including an amino acid sequence that has at least 40% (and preferably, 50%, 60%, 70%, 80%, or 90%) identity to the amino acid sequence of FIG. 7 (SEQ ID NO: 2) In preferred embodiments, the polypeptide is obtained from a cruciferous species, for example, *Arabidopsis thaliana*.

Exemplary plants which are useful in the methods of the invention, as well as for generating the transgenic plants (or plant cells, plant tissues, plant organs, or plant parts) of the invention, include, without limitation, dicots and monocots, such as sugar cane, wheat, rice, maize, sugar beet, barley, manioc, crucifer, mustard, potato, soybean, sorghum, cassava, banana, grape, oats, tomato, millet, coconut, papaya, orange, rye, cabbage, apple, eggplant, watermelon, canola, cotton, carrot, pepper, strawberry, peanut, legume, bean, pea, mango, and sunflower.

By "polypeptide" is meant any chain of amino acids, regardless of length or post-translational modification (for example, glycosylation or phosphorylation).

By "substantially identical" is meant a polypeptide or nucleic acid exhibiting at least 40%, preferably 50%, more preferably 80%, and most preferably 90%, or even 95% sequence identity to a reference sequence (for example, the amino acid sequences of the phosphatase domains or full-length dual-specificity MAPK phosphatases of MKP-1, MKP-2, MKP-3, MKP-4, PAC-1, MSG5, Pmp1, IphP, AtMKP-1, AtMKP-2, AtMKP-3, or AtMKP-4 or to their respective nucleic acid sequences). For polypeptides, the length of comparison sequences will generally be at least 16 amino acids, preferably at least 20 amino acids, more preferably at least 25 amino acids, and most preferably 35 amino acids or greater. For nucleic acids, the length of comparison sequences will generally be at least 50 nucleotides, preferably at least 60 nucleotides, more preferably at least 75 nucleotides, and most preferably 110 nucleotides or greater.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, FastA, or PILEUP/PRETTYBOX programs). Such software matches identical or similar sequences by assigning degrees of homology to various substitutions, deletions, and/or other modifications. Conservative substitutions typically include substitutions within the following groups: glycine alanine; valine, isoleucine, leucine; aspartic acid, glutamic acid, asparagine, glutamine; serine, threonine; lysine, arginine; and phenylalanine, tyrosine.

By a "substantially pure polypeptide" is meant a polypeptide (for example, a dual-specificity MAPK phosphatase) that has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, polypeptide. A substantially pure polypeptide may be obtained, for example, by extraction from a natural source (for example, a plant cell); by expression of a recombinant nucleic acid encoding the polypeptide; or by chemically synthesizing the protein. Purity can be measured by any appropriate method, for example, column chromatography, polyacrylamide gel electrophoresis, or by HPLC analysis.

By "specifically hybridizes" is meant that a nucleic acid sequence is capable of hybridizing to a DNA sequence at least under low stringency conditions as described herein, and preferably under high stringency conditions, also as described herein.

By "obtained from" is meant isolated from or having the sequence of a naturally-occurring sequence (e.g., a cDNA, genomic DNA, synthetic DNA, or combination thereof).

By "isolated nucleic acid molecule" is meant a nucleic acid (e.g., DNA) that is free of the genes which, in the naturally-occurring genome of the organism from which the nucleic acid of the invention is derived, flank the gene. The term therefore includes, for example, a gene or fragment thereof that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. It also includes a recombinant nucleic acid molecule which is part of a hybrid gene encoding additional polypeptide sequence.

By "transformed cell" is meant a cell into which (or into an ancestor of which) has been introduced, by means of recombinant DNA techniques, a DNA molecule encoding (as used herein) a dual-specificity MAPK phosphatase or a phosphatase domain-containing fragment thereof.

By "reporter gene" is meant a gene whose expression may be assayed; such genes include, without limitation, β-glucuronidase (GUS), luciferase (LUC), chloramphenicol transacetylase (CAT), green fluorescent protein (GFP), and β-galactosidase.

By "a promoter functional in a plant cell" is meant any minimal sequence sufficient to direct transcription in a plant cell. Included in the invention are promoter elements that are sufficient to render promoter-dependent gene expression controllable for cell-, tissue-, or organ-specific gene expression, or elements that are inducible by external signals or agents (for example, light-, pathogen-, wound-, stress-, or hormone-inducible elements or chemical inducers) or elements that are capable of cycling gene transcription; such elements may be located in the 5' or 3' regions of the native gene or engineered into a transgene construct.

By "operably linked" is meant that a gene and a regulatory sequence(s) are connected in such a way as to permit gene expression when the appropriate molecules (for example, transcriptional activator proteins) are bound to the regulatory sequence(s).

By "plant cell" is meant any self-propagating cell bounded by a semi-permeable membrane and containing a plastid. Such a cell also requires a cell wall if further propagation is desired. Plant cell, as used herein includes, without limitation, algae, cyanobacteria, seeds, suspension cultures, embryos, meristematic regions, callus tissue, leaves, roots, shoots, gametophytes, sporophytes, pollen, and microspores.

By "crucifer" is meant any plant that is classified within the Cruciferae family. The Cruciferae include many agricultural crops, including, without limitation, rape (for example, *Brassica campestris* and *Brassica napus*), broccoli, cabbage, brussel sprouts, radish, kale, Chinese kale, kohlrabi, cauliflower, turnip, rutabaga, mustard, horseradish, and Arabidopsis.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a nucleic acid sequence (e.g., a recombinant DNA sequence) which is inserted by artifice into a cell and becomes part of the genome of the organism which develops from that cell. As used herein, the transgenic organisms are generally transgenic plants and the DNA (transgene) is inserted by artifice into the nuclear or plastidic genome.

Other features and advantages of the invention will be apparent from the following description of the preferred embodiments thereof, and from the claims.

DETAILED DESCRIPTION

The drawings will first be described.

DRAWINGS

FIG. 1 is a photograph showing that MKP-1 transfected tobacco cells divide and differentiate at higher auxin levels than wild type control cells. Tobacco cells transfected with MKP-1 are shown on the left; wild type control cells transfected with vector alone are shown on the right.

FIG. 2 is a photograph showing that MKP-1 transformed SR1 tobacco produced about half the number of leaves before flowering as compared to the wild type plant. A flowering wild type plant is shown on the left. A flowering MKP-1 transformed tobacco plant is shown on the right.

Figure 5:
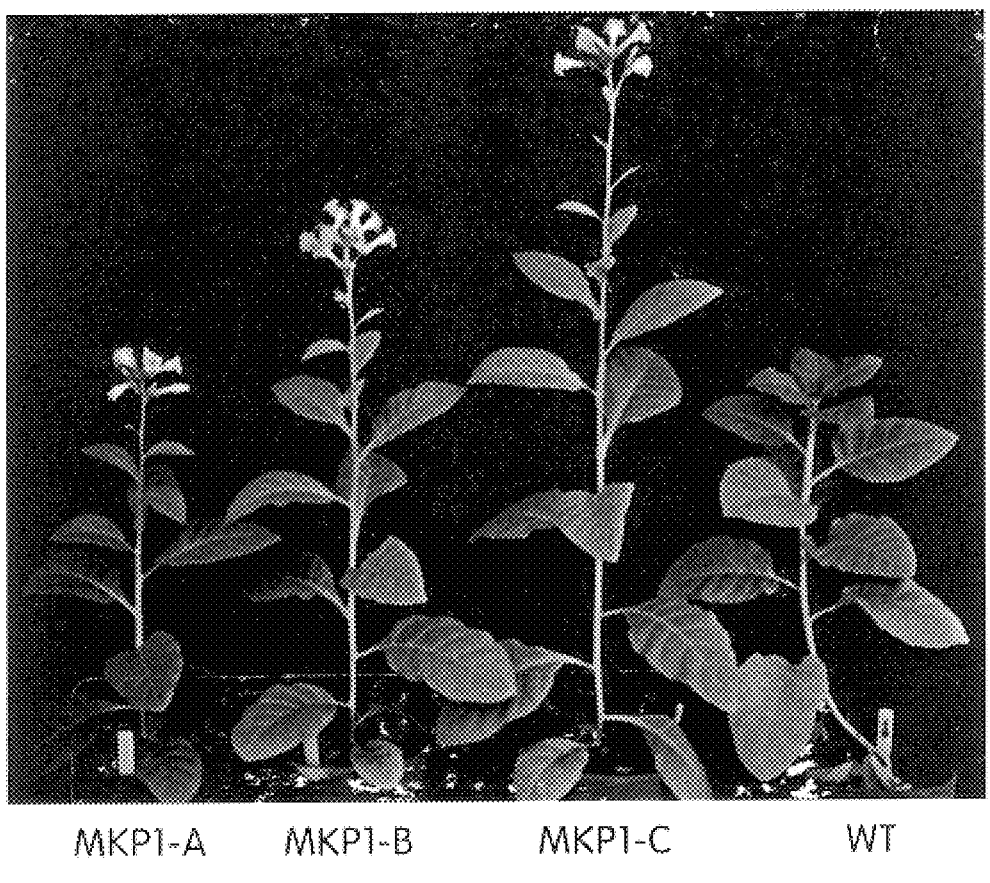

FIG. 5 is a photograph showing that progeny resulting from transgenic tobacco plants expressing MKP-1 flower earlier than wild type plants. Progeny MKP-1 transgenic lines (MKP-1A, MKP-1B, and MKP-1C) are shown on the left. A wild type plant is shown on the right.

Figure 6:

FIG. 6 is a photograph showing that transgenic tobacco plants expressing MKP-1 produce more flowers than wild type plants. A MKP-1 transgenic plant and a wild type plant are shown on the left and right, respectively.

FIG. 7 shows the nucleic acid sequence (SEQ ID NO: 1) and deduced amino acid sequence (SEQ ID NO: 2) of a dual-specificity MAPK phosphatase from Arabidopsis (AtMKP-1).

FIG. 8 is a diagram showing the alignment of the phosphatase domains of the dual-specificity MAPK phosphatases from human (MKP-1 (SEQ ID NO:7) and MKP-2 (SEQ ID NO:8)) and rat (MKP-3 (SEQ ID NO:9)) and homologous genes from Arabidopsis (At MKP-1 (SEQ ID NO:3), At MKP-2 (SEQ ID NO:4), At MKP-3 (SEQ ID NO: 5), and AtMKP-4 (SEQ ID NO:6)).

Below we present evidence that the expression of a phosphatase domain of a dual-specificity mitogen-activated protein kinase (MAPK) phosphatase generates plants having agronomically improved phenotypes. These examples are provided for the purpose of illustrating the invention, and should not be construed as limiting.

MKP-1 Expression in Transgenic Plant Cells and Plants

To investigate the role of MAPK pathways in plant growth and development, we perturbed the activation of endogenous MAP kinases by constitutively expressing a dual-specificity protein phosphatase, MKP-1, in both cultured plant cells and whole plants. MKP-1 is known to specifically inactivate MAP kinases in animal cells by dephosphorylating two key regulatory amino acid residues, threonine and tyrosine. Protein phosphatases that can specifically dephosphorylate/inactivate MAPKs have been reported in a variety of eukaryotes and are evolutionarily conserved (Tonks et al., Cell 87:365, 1996).

In transfected maize cells, MKP-1 was shown to specifically reverse the action of NPK1, a plant MAPK kinase kinase (MAPKKK), by inactivating its downstream MAPK. A phosphatase domain containing a fragment of the mouse MKP-1 (amino acids 1–314 (SEQ ID NO.: 11); Sun et al., *Cell* 75: 487–493, 1993) was cloned into the plant expression vector pART7. This expression plasmid was then used for transient expression of MKP-1 in maize protoplasts. The expression of MKP-1 under the control of the 35S CaMV promoter resulted in the complete elimination of the NPK1 effects, including the NPK1-dependent activation of a MAPK and the repression of the auxin-inducibility of the GH3 promoter. As controls, the expression of other plant protein phosphatases (PP) that belong to the three serine/threonine classes, PP1, PP2A, and PP2C, did not abolish the activation of MAPK by NPK1or the repression of the GH3 promoter by NPK1, despite the detection of enhanced PP activities in transfected maize protoplasts (Sheen, *EMBO J.* 12: 3497–3505, 1993; Sheen, *Proc. Natl. Acad. Sci. USA* 95: 975–980, 1998).

Figure 1:
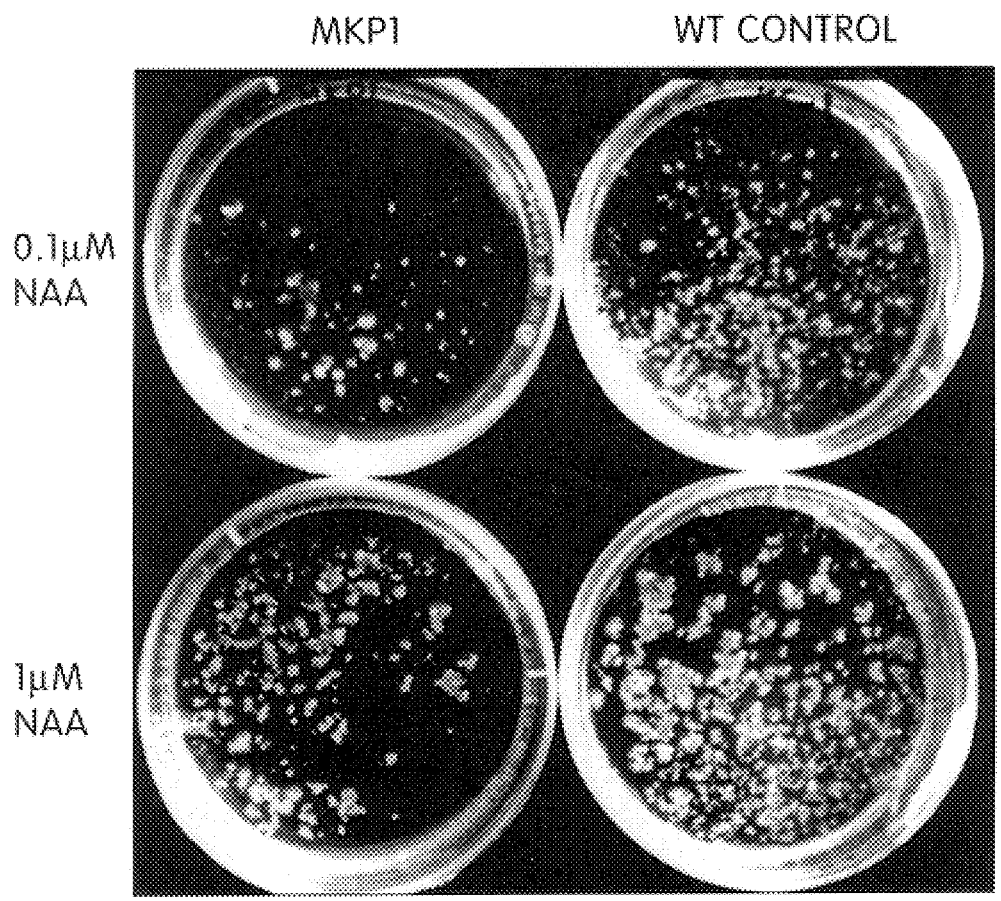

To examine the effects of auxin on cell division and differentiation of cells expressing MKP-1 SEQ ID NO.:10; tobacco cells transfected with the MKP-1 transgene expressed under the control of the 35S CaMV promoter were cultured on a medium containing 0.1 $\mu$M or 1 $\mu$M NAA. As shown in FIG. 1, under a constant concentration of cytokinin, cells which were transfected with MKP-1 required a higher level of auxin (1 $\mu$M NAA) to initiate cell division than cells trasfected with the vector alone. Although MKP-1 transfected cells failed to divide under a low concentration of auxin (0.1 $\mu$M NAA), cell division resumed when these cells were transferred to a medium with a higher level of auxin. Also, while the high level of auxin (1 $\mu$M NAA) was observed to support the proliferation of wild-type cells, MKP-1 transfected cells remained green and formed tight calli with differentiated shoot primordia (FIG. 1). Since prevention of MAPK activation by MKP-1 can render plant cells less sensitive to auxin, activation of some MAPK pathways may be crucial in auxin stimulated plant cell proliferation.

Figure 2:
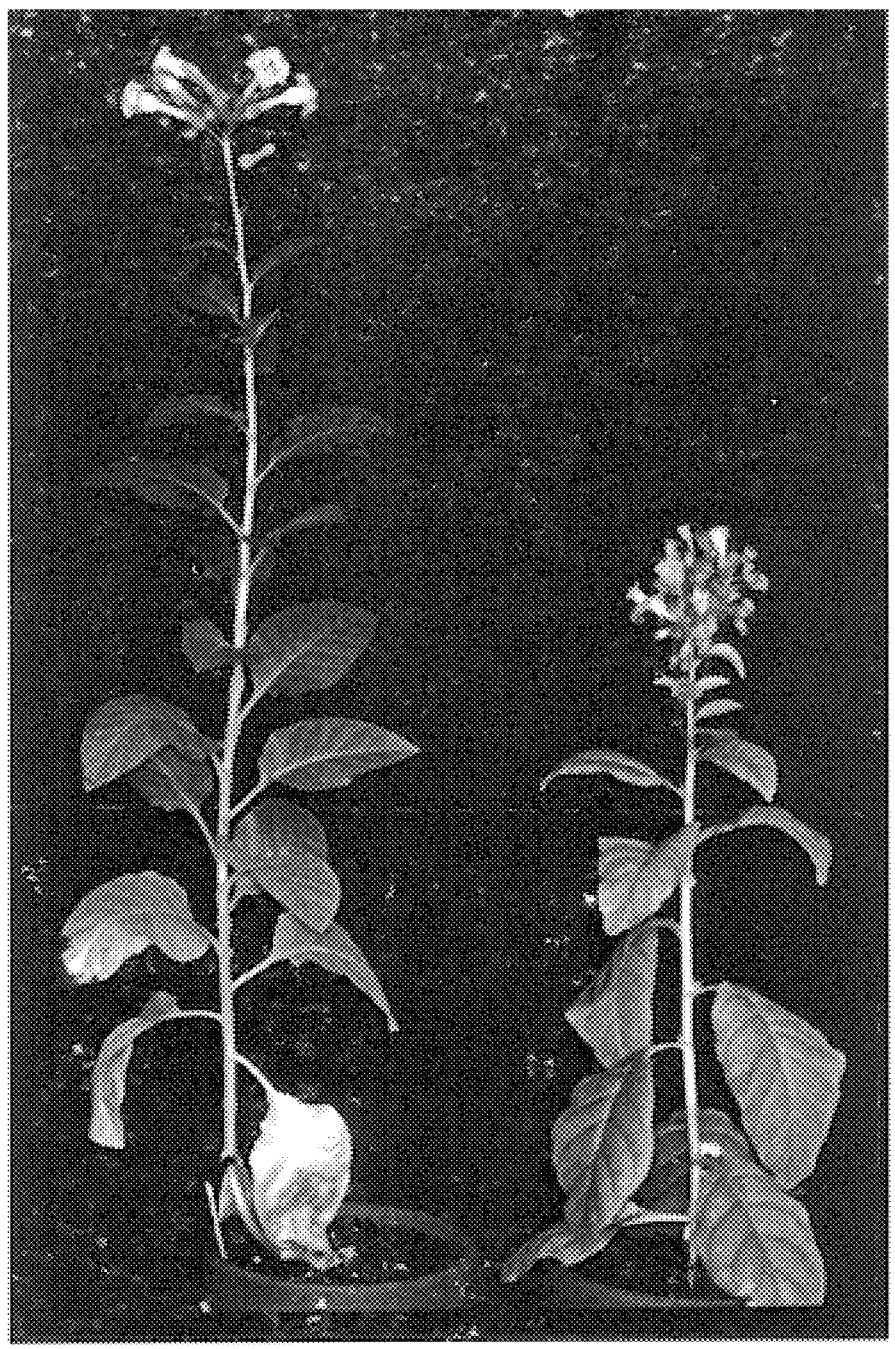
Figure 3:
FIG. 3 is a photograph showing that the expression of MKP-1 in transgenic tobacco plants promotes an early transition from the vegetative phase to reproductive phase. Six non-flowering wild type and six flowering transgenic plants are shown on the left and right, respectively.
Figure 4:
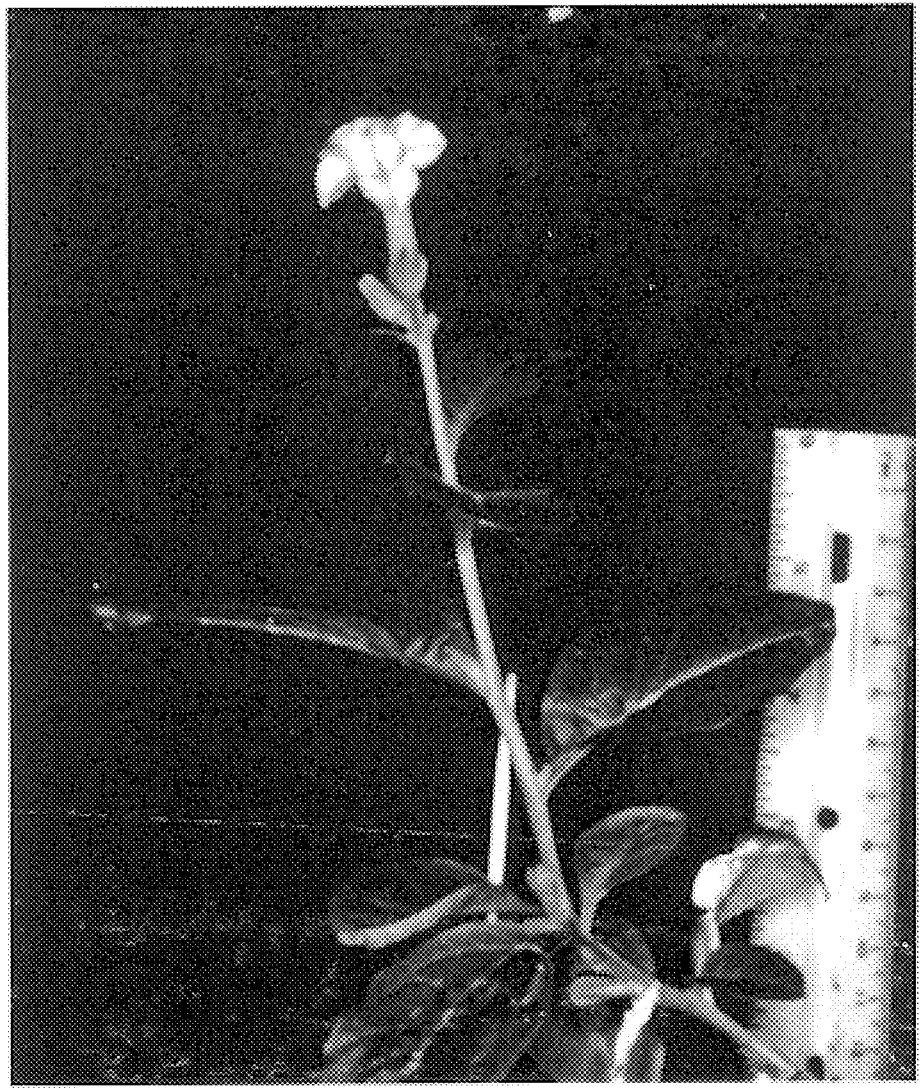
FIG. 4 is a photograph showing a six-inch tall flowering primary MKP-1 tobacco transformant.

Next, we examined the phenotypic modifications of transgenic plants expressing MKP-1 under the control of the 35S CaMV promoter. For these experiments, we introduced the MKP-1 construct into tobacco cultivar SR1 and Arabidopsis plants according to standard Agrobacterium-mediated gene transfer methods. Initiation of flowering in the day-neutral tobacco cultivar SR1 is mainly dependent on the number of leaves found on the plants. These tobacco plants, in general, remain in the vegetative state until approximately twenty leaves have developed. Unlike wild type SR1 plants, several primary transgenic SR1 lines expressing the MKP-1 transgene initiated flowering earlier than control plants (FIGS. 2 and 3). Some transformants even initiated flowers after only a few small leaves had developed (FIG. 4). Despite early flowering, these plants were fertile. In addition, the progenies obtained from the primary SR1 transformants were observed to initiate flower development after producing only 10 to 12 leaves (FIG. 5). Furthermore, the floral meristems of these transgenic plants were observed to remain active, producing additional flowers after setting seed. As a consequence, these transgenic plants produced more flowers and seeds than the wild-type plants (FIG. 6). Moreover, we observed that the expression of MKP-1 resulted in about a 50% reduction in the vegetative life span of the plant. Similar results were obtained when MKP-1 was expressed in Arabidopsis plants. Progenies obtained from several Arabidopsis lines which expressed the MKP-1 transgene under the control of the 35S CaMV promoter were also found to initiate the inflorescence stem without producing any rosette leaves. Although these plants exhibited little vegetative development, fully developed reproductive organs were produced and these organs were found fertile.

In sum, the results of our experiments indicate that plant and animal dual-specificity MAPK phosphatases have conserved sequences and function to inactivate MAPK signaling pathways which control and regulate meristem identity and its transition from the vegetative to floral state.

Additional Dual-Specificity MAPK Phosphatases

As indicated above, protein phosphatases that can specifically dephosphorylate/inactivate MAPKs have been reported in a variety of eukaryotes and are evolutionarily conserved (Tonks et al., *Cell* 8:7:365, 1996). Accordingly, a variety of dual-specificity MAPK phosphatases known in the art are useful for the production of transgenic plants having modified phenotypes. Exemplary dual-specificity MAPK phosphatases include, without limitation, PAC-1 (Ward et al., *Nature* 367:651–4, 1994), MKP-2 (Misra-Press et al., *Journal of Biological Chemistry* 270:14587–96, 1995), MKP-3 (Muda et al., *Journal of Biological Chemistry* 271:4319–26, 1996), MKP-4 (Muda et al., *Journal of Biological Chemistry* 272:5141–51, 1997), MSG5 (Doi et al., *EMBO J.* 13:61–70, 1994), Pmp1, (Sugiura et al., *EMBO J.* 17:140–8, 1998), and IphP (Potts et al., *Journal of Biological Chemistry* 68:7632–5, 1993). In addition, using standard cloning techniques, we have isolated a cDNA encoding a dual-specificity MAPK phosphatase (AtMKP1) from *Arabidopsis thaliana*. The nucleic acid sequence (SEQ ID NO: 1) and deduced amino acid sequence (SEQ ID NO: 2) encoded by this cDNA have been determined and are shown in FIG. 7. In addition, an alignment showing the conservation of amino acid residues of the phosphatase domains for several dual-specificity MAPK phosphatases is depicted in FIG. 8. This alignment was obtained using the Macaw computer program of the National Institute of Health, comparing the phosphatase domains of the dual-specificity MAPK phosphatases from human (MKP-1 (GenBank accession number NP 004408) and MKP-2 (GenBank accession number AAC50452)), rat (MKP-3 (GenBank accession number Q64346)), and homologous genes from Arabidopsis (At MKP-1 (infra), At MKP-2 (GenBank accession number AB023036), At MKP-3 (GenBank accession number AB013392), and AtMKP-4 (GenBank accession number AC006951)).

Isolation of Sequences Encoding Dual-Specificity MAPK Phosphatases

Any cell (eukaryotic or prokaryotic) can serve as the nucleic acid source for the molecular cloning of a dual-specificity MAPK phosphatase gene. The isolation of additional dual-specificity MAPK phosphatase coding sequences, as well as dual-specificity MAPK phosphatase domains, having the ability to regulate auxin responses and modify plant phenotypes is accomplished using standard strategies and techniques that are well known in the art. Based on the dual-specificity MAPK phosphatase genes and polypeptides described herein, the isolation of additional coding sequences is made possible using standard strategies and techniques that are well known in the art.

In one particular example, the mouse MKP-1 sequences described herein may be used, together with conventional screening methods of nucleic acid hybridization screening, to isolate additional sequences encoding dual-specificity MAPK phosphatase polypeptides (or phosphatase domain-containing fragments thereof), as well as phosphatase domains of dual-specificity MAPK phosphatase. Such hybridization techniques and screening procedures are well known to those skilled in the art and are described, for example, in Benton and Davis, *Science* 196:180, 1977; Grunstein and Hogness, *Proc. Natl. Acad. Sci., USA* 72:3961, 1975; Ausubel et al. *Current Protocols in Molecular Biology*, Wiley Interscience, New York; Berger and Kimmel, *Guide to Molecular Cloning Techniques*, 1987, Academic Press, New York.; and Sambrook et al., *Molecular Cloning: A Laboratory Manual*, Cold Spring Harbor Laboratory Press, New York. In one particular example, all or part of the MKP-1 gene may be used as a probe to screen a recombinant plant DNA library for genes having sequence identity or similarity to the MKP-1 gene or its phosphatase domain. Hybridizing sequences are detected by plaque or colony hybridization according to the methods described below.

Alternatively, using all or a portion of any one of the amino acid sequences of the phosphatase domains shown in FIG. 8, one may readily design phosphatase domain-specific oligonucleotide probes, including phosphatase domain degenerate oligonucleotide probes (i.e., a mixture of all possible coding sequences for a given amino acid sequence). These oligonucleotides may be based upon the sequence of either DNA strand and any appropriate portion of the phosphatase domain sequence. General methods for designing and preparing such probes are provided, for example, in Ausubel et al., *Current Protocols in Molecular Biology*, Wiley Interscience, New York; and Berger and Kimmel, *Guide to Molecular Cloning Techniques*, 1987, Academic Press, New York. These oligonucleotides are useful for phosphatase domain sequence isolation, either through their use as probes capable of hybridizing to phosphatase complementary sequences or as primers for various amplification techniques, for example, polymerase chain reaction (PCR) cloning strategies. If desired, a combination of different oligonucleotide probes may be used for the screening of a recombinant DNA library. The oligonucleotides may be detectably-labeled using methods known in the art and used to probe filter replicas from a recombinant DNA library. Recombinant DNA libraries are prepared according to methods well known in the art, for example, as described in Ausubel et al. (supra), or they may be obtained from commercial sources.

In one particular example of this approach, related dual-specificity MAPK phosphatase sequences having greater than 80% identity are detected or isolated using high stringency conditions. High stringency conditions may include hybridization at about 42° C. and about 50% formamide, 0.1 mg/mL sheared salmon sperm DNA, 1% SDS, 2×SSC, 10% Dextran sulfate, a first wash at about 65° C., about 2×SSC, and 1% SDS, followed by a second wash at about 65° C. and about 0. 1×SSC. Alternatively, high stringency conditions may include hybridization at about 42° C. and about 50% formamide, 0.1 mg/mL sheared salmon sperm DNA, 0.5% SDS, 5×SSPE, 1×Denhardt's, followed by two washes at room temperature and 2×SSC, 0.1% SDS, and two washes at between 55–60° C. and 0.2×SSC, 0.1% SDS.

In another approach, low stringency hybridization conditions for detecting dual-specificity MAPK phosphatase genes having about 40% or greater sequence identity to the genes described herein include, for example, hybridization at about 42° C. and 0.1 mg/mL sheared salmon sperm DNA, 1% SDS, 2×SSC, and 10% Dextran sulfate (in the absence of formamide), and a wash at about 37° C. and 6×SSC, about 1% SDS. Alternatively, the low stringency hybridization may be carried out at about 42° C. and 40% formamide, 0.1 mg/mL sheared salmon sperm DNA, 0.5% SDS, 5×SSPE, 1×Denhardt's, followed by two washes at room temperature and 2×SSC, 0.1% SDS and two washes at room temperature and 0.5×SSC, 0.1% SDS. These stringency conditions are exemplary; other appropriate conditions may be determined by those skilled in the art.

As discussed above, phosphatase domain-specific oligonucleotides may also be used as primers in amplification cloning strategies, for example, using PCR. PCR methods are well known in the art and are described, for example, in *PCR Technology,* Erlich, ed., Stockton Press, London, 1989; *PCR Protocols: A Guide to Methods and Applications,* Innis et al., eds., Academic Press, Inc., New York, 1990; and Ausubel et al. (supra). Primers are optionally designed to allow cloning of the amplified product into a suitable vector, for example, by including appropriate restriction sites at the 5' and 3' ends of the amplified fragment (as described herein). If desired, phosphatase domain sequences may be isolated using the PCR "RACE" technique, or Rapid Amplification of cDNA Ends (see, e.g., Innis et al. (supra)). By this method, oligonucleotide primers based on an phosphatase domain sequence are oriented in the 3' and 5' directions and are used to generate overlapping PCR fragments. These overlapping 3'- and 5'-end RACE products are combined to produce an intact full-length cDNA. This method is described in Innis et al. (supra); and Frohman et al., *Proc. Natl. Acad. Sci. USA* 85:8998, 1988.

Confirmation of a sequence's relatedness to the phosphatase domains of the dual-specificity MAPK phosphatases may be accomplished by a variety of conventional methods including, but not limited to, sequence comparison of the gene and its expressed product to a known MAPK phosphatase, e.g., those described herein. In addition, the activity of the gene product may be evaluated according to any of the techniques described.

Once a dual-specificity MAPK phosphatase gene or its phosphatase domain is identified, it is cloned according to standard methods and used for the construction of plant expression vectors as described below.

Expression Constructs

Those skilled in the field of molecular biology will understand that any of a wide variety of expression systems may be used to provide the recombinant protein. The precise host cell used is not critical to the invention. A dual-specificity MAPK phosphatase polypeptide or its phosphatase domain may be produced in a prokaryotic host, for example, *E. coli,* or in a eukaryotic host, for example, *Saccharomyces cerevisiae,* mammalian cells (for example, COS 1 or NIH 3T3 cells), or any of a number of plant hosts including, without limitation, algae, tree species, ornamental species, temperate fruit species, tropical fruit species, vegetable species, legume species, crucifer species, monocots, dicots, or in any plant of commercial or agricultural significance. Particular examples of suitable plant hosts include, but are not limited to, Conifers, Petunia, Tomato, Potato, Tobacco, Arabidopsis, Lettuce, Sunflower, Oilseed rape, Flax, Cotton, Sugarbeet, Celery, Soybean, Alfalfa, Medicago, Lotus, Vigna, Cucumber, Carrot, Eggplant, Cauliflower, Horseradish, Morning Glory, Poplar, Walnut, Apple, Grape, Asparagus, Rice, Maize, Millet, Onion, Barley, Orchard grass, Oat, Rye, and Wheat.

Materials for expressing these genes are available from a wide range of sources including the American Type Culture Collection (Rockland, Md.); or from any of a number seed companies, for example, W. Atlee Burpee Seed Co. (Warminster, Pa.), Park Seed Co. (Greenwood, S.C.), Johnny Seed Co. (Albion, Me.), or Northrup King Seeds (Harstville, S.C.). Descriptions and sources of useful host cells are also found in Vasil I.K., Cell Culture and Somatic Cell Genetics of Plants, Vol I, II, III Laboratory Procedures and Their Applications Academic Press, New York, 1984; Dixon, R. A., Plant Cell Culture-A Practical Approach, IRL Press, Oxford University, 1985; Green et al., Plant Tissue and Cell Culture, Academic Press, New York, 1987; and Gasser and Fraley, Science 244:1293, 1989.

The method of transformation or transfection and the choice of vehicle for expression of the dual-specificity MAPK phosphatase polypeptide or its phosphatase domain will depend on the host system selected. Transformation and transfection methods are described, e.g., in Ausubel et al. (supra); Weissbach and Weissbach, Methods for Plant Molecular Biology, Academic Press, 1989; Gelvin et al., Plant Molecular Biology Manual, Kluwer Academic Publishers, 1990; Kindle, K., *Proc. Natl. Acad. Sci., U.S.A* 87:1228, 1990; Potrykus, I., *Annu. Rev. Plant Physiol. Plant Mol. Biology* 42:205, 1991; and BioRad (Hercules, Calif.) Technical Bulletin #1687 (Biolistic Particle Delivery Systems). Expression vehicles may be chosen from those provided, e.g., in Cloning Vectors: A Laboratory Manual (P. H. Pouwels et al., 1985, Supp. 1987); Gasser and Fraley (supra); Clontech Molecular Biology Catalog (Catalog 1992/93 Tools for the Molecular Biologist, Palo Alto, Calif.); and the references cited above. Other expression constructs are described by Fraley et al. (U.S. Pat. No. 5,352,605).

Most preferably, a phosphatase domain of a dual-specificity MAPK phosphatase polypeptide is produced by a stably-transfected plant cell line, a transiently-transfected plant cell line, or by a transgenic plant. A number of vectors suitable for stable transfection of plant cells or for the establishment of transgenic plants are available to the public; such vectors are described in Pouwels et al. (supra), Weissbach and Weissbach (supra), and Gelvin et al. (supra). Methods for constructing such cell lines are described in, e.g., Weissbach and Weissbach (supra), and Gelvin et al. (supra). Typically, plant expression vectors include (1) a cloned gene under the transcriptional control of 5' and 3' regulatory sequences and (2) a dominant selectable marker. Such plant expression vectors may also contain, if desired, a promoter regulatory region (for example, one conferring inducible or constitutive, pathogen- or wound-induced, environmentally- or developmentally-regulated, or cell- or tissue-specific expression), a transcription initiation start site, a ribosome binding site, an RNA processing signal, a transcription termination site, and/or a polyadenylation signal.

Once the desired nucleic acid sequence encoding a domain of a dual-specificity MAPK phosphatase polypeptide is obtained as described above, it may be manipulated in a variety of ways known in the art. For example, where the sequence involves non-coding flanking regions, the flanking regions may be subjected to mutagenesis.

The nucleic acid molecule encoding the phosphatase domain of a dual-specificity MAPK phosphatase, if desired, may be combined with other DNA sequences in a variety of ways. Such a sequence may be employed with all or part of the gene sequences normally associated with itself. In its component parts, a DNA sequence encoding the dual-specificity MAPK phosphatase polypeptide is combined in a DNA construct having a transcription initiation control region capable of promoting transcription and translation in a host cell.

In general, the constructs will involve regulatory regions functional in plants which provide for modified production of the regulator protein as discussed herein. The open reading frame coding for the regulator protein or functional fragment thereof will be joined at its 5' end to a transcription initiation regulatory region such as the sequence naturally found in the 5' upstream region of the dual-specificity MAPK phosphatase polypeptide or its phosphatase domain. Numerous other transcription initiation regions are available which provide for constitutive or inducible regulation.

For applications where developmental, cell, tissue, hormonal, or environmental expression is desired, appropriate 5' upstream non-coding regions are obtained from other genes, for example, from genes regulated during meristem development, seed development, embryo development, or leaf development.

Regulatory transcript termination regions may also be provided in DNA constructs of this invention as well. Transcript termination regions may be provided by the DNA sequence encoding the dual-specificity MAPK phosphatase polypeptide or any convenient transcription termination region derived from a different gene source. The transcript termination region will contain preferably at least 1–3 kb of sequence 3' to the structural gene from which the termination region is derived. Plant expression constructs having, for example, a phosphatase domain of a dual-specificity MAPK phosphatase (e.g., MKP-1 or the Arabidopsis dual-specificity MAPK phosphatase (SEQ ID NO: 1)) as the DNA sequence of interest for expression may be employed with a wide variety of plant life. Such genetically-engineered plants are useful for a variety of industrial and agricultural applications as discussed herein. Importantly, this invention is applicable to dicotyledons and monocotyledons, and will be readily applicable to any new or improved transformation or regeneration method.

An example of a useful plant promoter according to the invention is a caulimovirus promoter, for example, a cauliflower mosaic virus (CaMV) promoter. These promoters confer high levels of expression in most plant tissues, and the activity of these promoters is not dependent on virally encoded proteins. CaMV is a source for both the 35S and 19S promoters. In most tissues of transgenic plants, the CaMV 35S promoter is a strong promoter (see, e.g., Odell et al., *Nature* 313:810, 1985). The CaMV promoter is also highly active in monocots (see, e.g., Dekeyser et al., Plant Cell 2:591, 1990; Terada and Shimamoto, *Mol. Gen. Genet.* 220:389, 1990). Moreover, activity of this promoter can be further increased (i.e., between 2–10 fold) by duplication of the CaMV 35S promoter (see e.g., Kay et al., *Science* 236:1299, 1987; Ow et al., *Proc. Natl. Acad. Sci., U.S.A.* 84:4870, 1987; and Fang et al., *Plant Cell* 1:141, 1989). In addition, a minimal 35S promoter may also be used as is described herein.

Other useful plant promoters include, without limitation, the nopaline synthase promoter (An et al., *Plant Physiol.* 88:547, 1988) and the octopine synthase promoter (Fromm et al., *Plant Cell* 1:977, 1989).

For certain applications, it may be desirable to produce a phosphatase domain of a dual-specificity MAPK phosphatase polypeptide in an appropriate tissue, at an appropriate level, or at an appropriate developmental time. For these purposes, there are an assortment of gene promoters, each with its own distinct characteristics embodied in its regulatory sequences, shown to be regulated in response to the environment, hormones, and/or developmental cues. These include gene promoters that are responsible for heat-regulated gene expression (see, e.g., Callis et al., *Plant Physiol.* 88:965, 1988; Takahashi and Komeda, *Mol. Gen. Genet.* 219:365, 1989; and Takahashi et al., *Plant J.* 2:751, 1992), light-regulated gene expression (e.g., the Arabidopsis Cab2 photosynthetic, leaf specific promoter described by Mitra et el., *Plant Mol. Biol.* 12: 169–179, 1989; the pea rbcS-3A described by Kuhlemeier et al., *Plant Cell* 1:471, 1989; the maize rbcS promoter described by Schäffner and Sheen, *Plant Cell* 3:997, 1991; or the cholorphyll a/b-binding protein gene found in pea described by Simpson et al., *EMBO J.* 4:2723, 1985), hormone-regulated gene expression (for example, the abscisic acid (ABA) responsive sequences from the Em gene of wheat described by Marcotte et al., *Plant Cell* 1:969, 1989; the ABA-inducible HVA1 and HVA22, and rd29A promoters described for barley and Arabidopsis by Straub et al., *Plant Cell* 6:617, 1994, Shen et al., Plant Cell 7:295, 1995; and wound-induced gene expression (for example, of wunI described by Siebertz et al., *Plant Cell* 1:961, 1989), organ-specific gene expression (for example, of the tuber-specific storage protein gene described by Roshal et al., *EMBO J.* 6:1155, 1987; the 23-kDa zein gene from maize described by Schemthaner et al., *EMBO J.* 7:1249, 1988; or the French bean B-phaseolin gene described by Bustos et al., *Plant Cell* 1:839, 1989; the vegetative storage protein promoter (soybean vspB) described by Sadka et al (*Plant Cell* 6: 737–749, 1994)), cycling promoters (e.g., the Arabidopsis cdc2a promoter described by Hemerly et al., *Proc Natl Acad Sci USA* 89: 3295–3299, 1992), senescence-specific promoters (e.g., the Arabidopsis SAG12 promoter described by Gan et al, *Science:* 270, 1986–1988, 1995), seed-specific promoters (for example, endosperm-specific or embryo-specific promoters), meristem-specific promoters (for example, the Tch4 promoter described by Xu et al., *Plant Cell* 7:1555–67, 1995), or pathogen-inducible promoters (for example, PR-1 or β-1,3 glucanase promoters).

Plant expression vectors may also optionally include RNA processing signals, e.g, introns, which have been shown to be important for efficient RNA synthesis and accumulation (Callis et al., *Genes and Dev.* 1:1183, 1987). The location of the RNA splice sequences can dramatically influence the level of transgene expression in plants. In view of this fact, an intron may be positioned upstream or downstream of a dual-specificity MAPK phosphatase polypeptide or its phosphatase-domain encoding sequence in the transgene to modulate levels of gene expression.

In addition to the aforementioned 5' regulatory control sequences, the expression vectors may also include regulatory control regions which are generally present in the 3' regions of plant genes (Thornburg et al., *Proc. Natl. Acad. Sci. U.S.A.* 84:744, 1987; An et al., *Plant Cell* 1:115, 1989). For example, the 3' terminator region may be included in the expression vector to increase stability of the mRNA. One such terminator region may be derived from the PI-II terminator region of potato. In addition, other commonly used terminators are derived from the octopine or nopaline synthase signals.

The plant expression vector also typically contains a dominant selectable marker gene used to identify those cells that have become transformed. Useful selectable genes for plant systems include genes encoding antibiotic resistance genes, for example, those encoding resistance to hygromycin, kanamycin, bleomycin, G418, streptomycin, or spectinomycin. Genes required for photosynthesis may also be used as selectable markers in photosynthetic-deficient strains. Finally, genes encoding herbicide resistance may be used as selectable markers; useful herbicide resistance genes include the bar gene encoding the enzyme phosphinothricin acetyltraxisferase and conferring resistance to the broad spectrum herbicide BASTA® (glufosinate) (Hoechst AG, Frankfurt, Germany).

Efficient use of selectable markers is facilitated by a determination of the susceptibility of a plant cell to a particular selectable agent and a determination of the concentration of this agent which effectively kills most, if not all, of the transformed cells. Some useful concentrations of antibiotics for tobacco transformation include, e.g., 75–100 µg/mL (kanamycin), 20–50 µg/m:L (hygromycin), or 5–10 µg/mL (bleomycin). A useful strategy for selection of transformants for herbicide resistance is described, e.g., by Vasil et al., supra.

It should be readily apparent to one skilled in the art of molecular biology, especially in the field of plant molecular biology, that the level of gene expression is dependent, not only on the combination of promoters, RNA processing signals, and terminator elements, but also on how these elements are used to increase the levels of selectable marker gene expression.

Plant Transformation

Upon construction of the plant: expression vector, several standard methods are available for introduction of the vector into a plant host, thereby generating a transgenic plant. These methods include (1) Agrobacterium-mediated transformation (*A. tumefaciens* or *A. rhizogenes*) (see, e.g., Lichtenstein and Fuller, In: Genetic Engineering, vol 6, PWJ Rigby, ed, London, Academic Press, 1987; and Lichtenstein, C. P., and Draper, J,. In: *DNA Cloning*, Vol II, D. M. Glover, ed, Oxford, IRI Press, 1985)), (2) the particle delivery system (see, e.g., Gordon-Kamm et al., *Plant Cell* 2:603, 1990); or BioRad Technical Bulletin 1687, supra), (3) microinjection protocols (see, e.g., Green et al., supra), (4) polyethylene glycol (PEG) procedures (see, e.g., Draper et al., *Plant Cell* Physiol. 23:451, 1982; or e.g., Zhang and Wu, *Theor. Appl. Genet.* 76:835, 1988), (5) liposome-mediated DNA uptake (see, e.g., Freeman et al., *Plant Cell Physiol.* 25:1353, 1984), (6) electroporation protocols (see, e.g., Gelvin et al., supra; Dekeyser et al., supra; Fromm et al., *Nature* 319:791, 1986; *Sheen*, Plant Cell 2:1027, 1990; or Jang and Sheen, *Plant Cell* 6:1665, 1994), and (7) the vortexing method (see, e.g., Kindle supra). The method of transformation is not critical to the invention. Any method which provides for efficient transformation may be employed. As newer methods are available to transform crops or other host cells, they may be directly applied.

The following is an example outlining one particular technique, an Agrobacterium-mediated plant transformation. By this technique, the general process for manipulating genes to be transferred into the genome of plant cells is carried out in two phases. First, cloning and DNA modification steps are carried out in *E. coli*, and the plasmid containing the gene construct of interest is transferred by conjugation or electroporation into Agrobacterium. Second, the resulting Agrobacterium strain is used to transform plant cells. Thus, for the generalized plant expression vector, the plasmid contains an origin of replication that allows it to replicate in Agrobacterium and a high copy number origin of replication functional in *E. coli*. This permits facile production and testing of transgenes in *E. coli* prior to transfer to Agrobacterium for subsequent introduction into plants. Resistance genes can be carried on the vector, one for selection in bacteria, for example, streptomycin, and another that will function in plants, for example, a gene encoding kanamycin resistance or herbicide resistance. Also present on the vector are restriction endonuclease sites for the addition of one or more transgenes and directional T-DNA border sequences which, when recognized by the transfer functions of Agrobacterium, delimit the DNA region that will be transferred to the plant.

In another example, plant cells may be transformed by shooting into the cell tungsten microprojectiles on which cloned DNA is precipitated. In the Biolistic Apparatus (Bio-Rad) used for the shooting, a gunpowder charge (22 caliber Power Piston Tool Charge) or an air-driven blast drives a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to pass through. As a result, the plastic macroprojectile smashes against the stopping plate, and the tungsten microprojectiles continue toward their target through the hole in the plate. For the instant invention the target can be any plant cell, tissue, seed, or embryo. The DNA introduced into the cell on the microprojectiles becomes integrated into either the nucleus or the chloroplast.

In general, transfer and expression of transgenes in plant cells are now routine practices to those skilled in the art, and have become major tools to carry out gene expression studies in plants and to produce improved plant varieties of agricultural or commercial interest.

Transgenic Plant Regeneration

Plant cells transformed with a plant expression vector can be regenerated, for example, from single cells, callus tissue, or leaf discs according to standard plant tissue culture techniques. It is well known in the art that various cells, tissues, and organs from almost any plant can be successfully cultured to regenerate an entire plant; such techniques are described, e.g., in Vasil supra; Green et al., supra; Weissbach and Weissbach, supra; and Gelvin et al., supra.

In one particular example, a cloned phosphatase domain of a dual-specificity MAPK phosphatase (or a dual-specificity MAPK phosphatase polypeptide or a phosphatase-containing fragment thereof) construct under the control of the nos promoter and the nopaline synthase terminator and carrying a selectable marker (for example, kanamycin resistance) is transformed into Agrobacterium. Transformation of leaf discs (for example, of tobacco or potato leaf discs), with vector-containing Agrobacterium is carried out as described by Horsch et al. (*Science* 227:1229, 1985). Putative transformants are selected after a few weeks (for example, 3 to 5 weeks) on plant tissue culture media containing kanamycin (e.g. 100 µg/mL). Kanamycin-resistant shoots are then placed on plant tissue culture media without hormones for root initiation. Kanamycin-resistant plants are then selected for greenhouse growth. If desired, seeds from self-fertilized transgenic plants can then be sowed in a soil-less medium and grown in a greenhouse. Kanamycin-resistant progeny are selected by sowing surfaced sterilized seeds on hormone-free kanamycin-containing media. Analysis for the integration of the transgene is accomplished by standard techniques (see, for example, Ausubel et al. supra; Gelvin et al. supra).

Transgenic plants expressing the selectable marker are then screened for transmission of the transgene DNA by standard immunoblot and DNA detection techniques. Each positive transgenic plant and its transgenic progeny are unique in comparison to other transgenic plants established with the same transgene. Integration of the transgene DNA into the plant genomic DNA is in most cases random, and the site of integration can profoundly affect the levels and the tissue and developmental patterns of transgene expression. Consequently, a number of transgenic lines are usually screened for each transgene to identify and select plants with the most appropriate expression profiles.

Transgenic lines are evaluated for levels of transgene expression. Expression at the RNA level is determined initially to identify and quantitate expression-positive plants. Standard techniques for RNA analysis are employed and include PCR amplification assays using oligonucleotide primers designed to amplify only transgene RNA templates and solution hybridization assays using transgene-specific probes (see, e.g., Ausubel et al., supra). The RNA-positive plants are then analyzed for protein expression by Western immunoblot analysis using specific antibodies (see, e.g., Ausubel et al., supra). In addition, in situ hybridization and immunocytochemistry according to standard protocols can be done using transgene-specific nucleotide probes and antibodies, respectively, to localize sites of expression within transgenic tissue.

In addition, if desired, once the recombinant dual-specificity MAPK phosphatase polypeptide or its phosphatase domain is expressed in any cell or in a transgenic plant (for example, as described above), it may be isolated, e.g., using affinity chromatography. In one example, an anti-dual-specificity MAPK phosphatase polypeptide antibody (e.g., produced as described in Ausubel et al., supra, or by any standard technique) may be attached to a column and used to isolate the polypeptide. Lysis and fractionation of dual-specificity MARK phosphatase-producing cells prior to affinity chromatography may be performed by standard methods (see, e.g., Ausubel et al., supra). Once isolated, the recombinant protein can, if desired, be further purified, for example, by high performance liquid chromatography (see, e.g., Fisher, Laboratory Techniques In Biochemistry And Molecular Biology, eds., Work and Burdon, Elsevier, 1980).

Engineering Novel Phenotypes

As discussed above, by expressing a phosphatase domain of a dual-specificity MAPK phosphatase, we have engineered plants that flower earlier, have expanded reproductive activity, reduced vegetative growth, delayed senescence, reduced plant size, and increased numbers of flowers and seeds. Accordingly, plant expression constructs designed for the expression of a phosphatase domain of a dual-specificity MAPK phosphatase are useful for generating transgenic plants having such phenotypes. To engineer such plants, it is important to express the phosphatase domain at an effective level. This is readily accomplished using standard plant gene promoters known in the art. For example, the 35S CaMV and TCH4 gene promoters are respectively useful for the constitutive and inducible expression of the phosphatase throughout a plant, and especially in the meristems. Evaluation of the phenotype conferred to a plant by expression of a DNA sequence expressing a phosphatase domain of a dual-specificity MAPK phosphatase polypeptide is then determined according to conventional methods and assays, for example, as described below.

Shortened Time Period to Reach Reproductive Capacity

In one working example, meristem-specific expression of a phosphatase domain of a dual-specificity MAPK phosphatase, for example, MKP-1, is used in rape to shorten the plant's life cycle. For example, a plant expression vector is constructed that contains the MKP-1 sequence expressed under the control of the Tch4 gene promoter described by Xu et al. (*Plant Cell* 7: 1555–67, 1995). This expression vector is then used to transform rape according to standard methods. To assess generation time, transformed rape plants and appropriate controls are evaluated according to standard methods. For example, growth and physiological measurements may be used to document the differences between transgenic and control plants. Additionally, transgenic plants expressing a recombinant dual-specificity MAPK phosphatase domain are evaluated for the time required to produce flowers. Plants expressing such polypeptides generally will require less time to flower when compared to control non-transformed plants. By decreasing the time needed to flower, the growing season of crop plants are shortened and more photosynthetic energy is committed to the production of fruits and seeds as the senescence of mature leaves is delayed. Transformed rape plants having shorter life cycles relative to control plants are taken as being useful in the invention.

Prolonged Flower Production

Transgenic plants expressing a recombinant dual-specificity MAPK phosphatase domain may also be evaluated in artificial environments or in the field to demonstrate that the transgene confers the ability to produce flowers during the majority of the life cycle of the plant. Transgenic plants having an increased ability to sustain flower production, as compared to non-transgenic plants, are useful in the invention.

Increased Seed Production

To demonstrate that expression of a phosphatase domain confers increased seed production, transgenic plants expressing a recombinant phosphatase domain of a dual-specificity MAPK phosphatase polypeptide may be evaluated for the ability to produce an increased number of seeds.

Increased Yield/Productivity

To test for increased yield or productivity, seeds of transgenic plants expressing a recombinant phosphatase domain of a dual-specificity MAPK phosphatase may be planted out in test plots, and their agronomic performance compared to standard plants using techniques familiar to those of skill in the art. Optionally included in this comparison are plants of similar genetic background lacking the transgene. If a yield benefit is observed, plants exhibiting the increased yield are advanced for commercialization.

In addition, transgenic plants expressing a recombinant phosphatase domain may be field tested for agronomic performance. When compared to nontransgenic plants, transgenic plants expressing the phosphatase domain exhibit higher yield than their non-transgenic counterparts under similar growing conditions.

Increased Regeneration Capacity

While auxin is required to maintain the proliferation of plant cells in tissue culture, its presence inhibits plant cell differentiation, a necessary step for plant regeneration. Constitutive expression of a recombinant phosphatase domain of a dual-specificity MAPK phosphatase is useful to eliminate the inhibitory effects of auxin and to facilitate plant regeneration in tissue culture. Transgenic plants expressing a recombinant phosphatase domain of a MAPK phosphatase: may be tested for plant regeneration performance under conditions, including, but not limited to, high auxin levels (for example, 1.0 μM). When compared to nontransgenic plants, transgenic plants expressing the phosphatase domain exhibit higher yields of regenerated plantlets than their non-transgenic counterparts under such tissue culture conditions.

Use

The invention described herein is useful for a variety of agricultural and commercial purposes including, but not limited to, increasing crop yields, improving crop and ornamental quality, and reducing agricultural production costs. In particular, ectopic expression of a phosphatase domain of a dual-specificity MAPK phosphatase polypeptide (or a dual-specificity MAPK phosphatase polypeptide or a phosphatase domain-containing fragment thereof) causes the plant to flower sooner, leading to shorter generation times which have economic advantages for crop plants. By shortening plant life span, the invention also facilitates the production of new varieties through breeding or genetic engineering of tree species or crop plants having long juvenile phases (e.g., those tree species having juvenile phases of about 5–20 years).

In particular, ectopic expression of a phosphatase domain of a MAPK phosphatase (or a MAPK polypeptide or a phosphatase domain-containing fragment thereof) in a plant cell is useful for modifying the phenotype. The invention therefore provides for modification of a plant's phenotype, especially crop plants, most especially crop plants such as tomato, potato, cotton, pepper, maize, wheat, rice, and legumes such as soybean, or any crop plant that is susceptible to an adverse stress. For example, transgenic maize and soybean may be genetically engineered to express a phosphatase domain of a MAPK phosphatase (e.g., MKP-1, MKP-2, MKP-3, MKP-4, PAC-1, MSG5, Pmp1, IphP, AtMKP1, AtMKP2, AtMKP3, or AtMKP4) according to standard methods, such as those described in Adams et al. (U.S. Pat. No. 5,550,318) and Collins et al. (U.S. Pat. No. 5,024,944). Methods for transforming wheat with such genes are described in Fry et al. (U.S. Pat. No. 5,631,152).

OTHER EMBODIMENTS

The invention further includes the use of analogs of any naturally-occurring dual-specificity MAPK phosphatase polypeptide. Analogs can differ from the naturally-occurring phosphatase domain by amino acid sequence differences, by post-translational modifications, or by both. Analogs of the invention will generally exhibit at least 40%, more preferably 50%, and most preferably 60% or even having 70%, 80%, or 90% identity with all or part of a naturally-occurring phosphatase domain amino acid sequence. The length of sequence comparison is at least 15 amino acid residues, preferably at least 25 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring phosphatase domain polypeptide by alterations in primary sequence. These include genetic variants, both natural and induced (for example, resulting from random mutagenesis by irradiation or exposure to ethyl methylsulfate or by site-specific mutagenesis as described in Sambrook, Fritsch and Maniatis, *Molecular Cloning: A Laboratory Manual* (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., β or γ amino acids.

In addition, the invention also includes phosphatase domain fragments. Exemplary phosphatase domains of about 87 amino acids or about 80 amino acids that are useful for generating fragments of a phosphatase domain are shown in FIG. 8. As used herein, the term "fragment," means at least 20 contiguous amino acids, preferably at least 40 contiguous amino acids, more preferably at least 80 contiguous amino acids, and most preferably at least 85 or more contiguous amino acids. Fragments of phosphatase domain polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events). In preferred embodiments, a phosphatase domain fragment (e.g., a fragment of any of the dual-specificity MAPK phosphatases described herein) is capable of inactivating a MAPK signal pathway and modifying a plant's phenotype. Methods for evaluating such activity are described herein.

All publications and patent applications mentioned in this specification are herein incorporated by reference to the same extent as if each independent publication or patent application was specifically and individually indicated to be incorporated by reference.

What is claimed is:

1. A method for increasing flower production of a plant, said method comprising the steps of:
   (a) introducing into one or more plant cells ; transgene comprising DNA encoding a phosphatase domain of a dual-specificity mitogen-activating protein kinase phosphatase 1 (MKP-1) operably linked to a promoter functional in said plant cell(s), to yield one or more transformed plant cells; and
   (b) regenerating a transgenic plant from one or more said transformed plant cells, wherein the phosphatase domain of said dual-specificity MKP-1 is expressed in the cells of said transgenic plant, and wherein expression of said DNA encoding said phosphatase domain of said dual-specificity MKP-1 increases flower production of said transgenic plant relative to a control plant.

2. A method for promoting early flowering of a plant, said method comprsing the steps of:
   (a) introducing into one or more plant cells a transgene comprising DNA encoding a phosphatase domain of a dual-specificity mitogen-activating protein kinase phosphatase 1 (MKP-1) operably linked to a promoter functional in said plant cell(s), to yield one or more transformed plant cells; and
   (b) regenerating a transgenic plant from one or more said transformed plant cells, wherein the phosphatase domain of said dual-specificity MKP-1 is expressed in the cells of said transgenic plant, and wherein expression of said DNA encoding said phosphatase domain of said dual-specificity MKP-1 promotes early flowering of said transgenic plant.

3. A method for increasing the reproductive life cycle of a plant, said method comprising the steps of:
   (a) introducing into one or more plant cells a transgene comprising DNA encoding a phosphatase domain of a dual-specificity mitogen-activating protein kinase phosphatase 1 (MKP-1) operably linked to a promoter functional in said plant cell(s), to yield one or more transformed plant cells; and
   (b) regenerating a transgenic plant from one or more said transformed plant cells, wherein the phosphatase domain of said dual-specificity MKP-1 is expressed in the cells of said transgenic plant, and wherein expression of said DNA encoding said phosphatase domain of said dual-specificity MKP-1 increases the reproductive life cycle of said transgenic plant relative to a control plant.

4. A method for decreasing the vegetative growth of a plant, said method comprising the steps of:
   (a) introducing into one or more plant cells a transgene comprising DNA encoding a phosphatase domain of a dual-specificity mitogen-activating protein kinase phosphatase 1 (MKP-1) operably linked to a promoter functional in said plant cell(s), to yield one or more transformed plant cells; and
   (b) regenerating a transgenic plant from one or more said transformed plant cells, wherein the phosphatase domain of said dual-specificity MKP-1 is expressed in the cells of said transgenic plant, and wherein expression of said DNA encoding said phosphatase domain of said dual-specificity MKP-1 decreases the vegetative growth of said transgenic plant relative to a control plant.

5. A method for shortening the time to reproductive capacity of a plant, said method comprising the steps of:
   (a) introducing into one or more plant cells a transgene comprising DNA encoding a phosphatase domain of a dual-specificity mitogen-activating protein kinase phosphatase 1 (MKP-1) operably linked to a promoter functional in said plant cell(s), to yield one or more transformed plant cells; and
   (b) regenerating a transgenic plant from one or more said transformed plant cells, wherein the phosphatase domain of said dual-specificity MKP-1 is expressed in the cells of said transgenic plant and wherein expression of said DNA encoding said phosphatase domain of said dual-specificity MKP-1 shortens the time to reproductive capacity of said transgenic plant relative to a control plant.

6. A method for decreasing the auxin sensitivity of a plant, said method comprising the steps of:
   (a) introducing into one or more plant cells a transgene comprising DNA encoding a phosphatase domain of a dual-specificity mitogen-activating protein kinase phosphatase 1 (MKP-1) operably linked to a promoter functional in said plant cell(s), to yield one or more transformed plant cells; and
   (b) regenerating a transgenic plant from one or more said transformed plant cells, wherein the phosphatase domain of said dual-specificity MKP-1 is expressed in the cells of said transgenic plant, and wherein expression of said DNA encoding said phosphatase domain of said dual-specificity MKP-1 decrease(s the auxin sensitivity of said transgenic plant relative to a control plant.

7. A method for increasing seed production of a plant, said method comprising the steps of:
(a) introducing into one or more plant cells a transgene comprising DNA encoding a phosphatase domain of a dual-specificity mitogen-activating protein kinase phosphatase 1 (MKP-1) operably linked to a promoter functional in said plant cell(s), to yield one or more transformed plant cells; and
(b) regenerating a transgenic plant from one or more said transformed plant cells, wherein the phosphatase domain of said dual-specificity MKP-1 is expressed in the cells of said transgenic plant, and wherein expression of said DNA encoding said phosphatase domain of said dual-specificity MKP-1 increases seed production of said transgenic plant relative to a control plant.

8. The method of any one of claims 1–7 wherein said dual-specificity MKP-1 hydrolyzes phosphoserine/threonine and phosphotyrosine residues on a protein substrate.

9. The method of any one of claims 1–7, wherein said eukaryotic dual-specificity MKP-1 comprises amino acids 1–314 of MKP-1 (SEQ ID NO:11).

10. The method of any one of claims 1–7, wherein said DNA encoding said phosphatase domain of said dual-specificity MKP-1 is constitutively expressed.

11. The method of any one of claims 1–7, wherein said DNA encoding said phosphatase domain of said dual-specificity MKP-1 is inducibly expressed.

12. The method of any one of claims 1–7 wherein said DNA encoding said phosphatase domain of said dual-specificity MKP-1 is expressed in a cell-specific, tissue-specific, or organ-specific manner.

13. The method of any cone of claims 1–7, wherein said DNA encodes a polypeptide consisting essentially of said phosphatase domain.

14. A plant comprising a transgene that expresses a phosphatase domain of a dual-specificity MKP-1, wherein said transgene is expressed in said transgenic plant under the control of a promoter that is functional in a plant cell.

15. The plant of claim 14, wherein said dual-specificity MKP-1 hydrolyzes phosphoserine/threonine and phosphotyrosine residues on a protein substrate.

16. The plant of claim 14, wherein said eukaryotic dual-specificity MKP-1 comprises amino acids 1–314 of MKP-1 (SEQ ID NO:11).

17. The plant of claim 14, wherein said transgene encodes a phosphatase domain of said dual-specificity MKP-1 which is constitutively expressed.

18. The plant of claim 14, wherein said transgene encodes a phosphatase domain of said dual-specificity MKP-1 which is inducibly expressed.

19. The plant of claim 14, wherein said transgene encodes a phosphatase domain of said dual-specificity MKP-1 which is expressed in a cell-specific, tissue-specific, or organ-specific manner.

20. The plant of claim 14, wherein said transgene encodes a polypeptide consisting of said phosphatase domain.

21. The plant of claim 14, wherein said plant is a dicot.

22. The plant of claim 14, wherein said plant is a monocot.

23. A seed from the plant of claim 14, wherein the seed comprises the transgene.

24. A cell from the plant of claim 14.

* * * * *

UNITED STATES PATENT AND TRADEMARK OFFICE
CERTIFICATE OF CORRECTION

PATENT NO. : 6,548,743 B1
DATED : April 15, 2003
INVENTOR(S) : Sheen et al.

It is certified that error appears in the above-identified patent and that said Letters Patent is hereby corrected as shown below:

Title page,
Item [56], References Cited, OTHER PUBLICATIONS, "Kato et al." reference, "Requred" should be -- Required --;
"Machida et al." reference, "Progess" should be -- Progress --;
"Posas et al." reference, "Resposne" should be -- Response --.

Column 2,
Line 44, "AtMKP3 or AtMKP3" should be -- AtMKP3 or AtMKP4 --.

Column 3,
Line 59, "glycine alanine" should be -- glycine, alanine --.

Column 5,
Line 67, "At MKP-1" should be -- AtMKP-1 --.

Column 5, line 67 through Column 6, line 1,
"At MKP-2" should be -- AtMKP-2 --.

Column 6,
Line 1, "At MKP-3" should be -- AtMKP-3 --; and
Line 49, "trasfected" should be -- transfected --.

Column 7,
Line 64, "At MKP-1" should be -- AtMKP-1 --; and "At MKP-2" should be -- AtMKP-2 --.

Column 29,
Line 25, ";" should be -- a --; and
Line 38, "comprsing" should be -- comprising --.

Column 31,
Line 1, decrease (s" should be -- decreases --.

UNITED STATES PATENT AND TRADEMARK OFFICE
CERTIFICATE OF CORRECTION

PATENT NO.    : 6,548,743 B1
DATED         : April 15, 2003
INVENTOR(S)   : Sheen et al.

It is certified that error appears in the above-identified patent and that said Letters Patent is hereby corrected as shown below:

Column 32,
Line 1, "cone" should be -- one --.

Signed and Sealed this

Fourteenth Day of December, 2004

JON W. DUDAS
*Director of the United States Patent and Trademark Office*

SEQUENCE LISTING

```
<160> NUMBER OF SEQ ID NOS: 11

<210> SEQ ID NO 1
<211> LENGTH: 1444
<212> TYPE: DNA
<213> ORGANISM: Arabidopsis thaliana
<220> FEATURE:
<221> NAME/KEY: variation
<222> LOCATION: (1)...(1444)
<223> OTHER INFORMATION: n is any nucleotide or absent.

<400> SEQUENCE: 1
```

-continued

```
atgtatatca aagaactgac ggaaacggat gaggagaaga gggagagatc ggttgaggat     60
aacgtngatg atggagataa ggcggtattg gtgagcagag gaaacgtgat tgtgtcgact    120
acaaagaggg cactcgttgg tgttggtgct cgtgctttgt tttatcctac tctggtttac    180
aacgttgtta ggaataagct cgaatctgag tttcgctggt gggatcgcgt ggctgagttt    240
atattactgg gagctgttcc atttccatct gatgttccac agctgaaaga nctcggtgtt    300
tgtggagtga tcactctgaa tgagccatat gaaactttgg ttccatcgtc tctctacaaa    360
tcttactgca ttgaccacct ggtgattgct acaagaaatt attgttttgc tccttccatg    420
gaagcaatat gccaagctgt agaatttatc catagaaatg cttcgcttgg aaagacgact    480
tatgttcact gcaaagcggg tcggggtcgc agcacaacta ttttcatatg ttacttggtt    540
caacacaaaa acatgacacc tgaagcagca tattcntacg tgagatcaat caggcccagg    600
gttcttttag cagcagccca atggaaggcc gttgttgagt actaccatgt caaggtgctg    660
aatactcaga gttgcttaac tgatgcaact tcagctttga tcccaagaaa tgtgaagcag    720
gtttgttctg ggaatgtagt ggtgtttgat gatgggtcaa tggttgtagt cacccactcg    780
gatctagagg gctataatga tgatgactca cggtcacgga ggtcagtgaa agttaatggg    840
aatgagctat gggcggcagc tgcagatctg agtatggtgt acaggggtgaa agtggtgggg    900 caggctgcga tggcgaggat atcgtgtctg tggctgggct tgcgtgagga ccaaaagctt    960
tctgggaaaa atctttccat gggaggcata agcgtcgaca tttctgtcta ctgatgatga   1020
tggcgaagaa tgaatgcagg tgagtctgct ggcgagtgag tgaatatacc ttattcactg   1080
tttctcccca gtagaaaaaa aaagtctcta aataaaaaaa tgggtcaaat taggtataga   1140
agtaagcaag ggtttgtaaa tttgaaaaaa aaaaaaaact tggttttgtc gtctgggtat   1200
tgtaattaaa tactaccttg tccctcattt gcctttgatg aggataaaca tgaattagtc   1260
tctaaaaaaa aaactaaatt actcacactg gcggccgctc tagaactagt ggatccccg    1320 ggctgcagga attcgatatc aagtttatcg ataccgtcga cctcgagggg gggcccggta   1380
ccagcttttg ttccttttta gtgagggtga atttcgagct tgntgtaatc aggctcatag   1440
ctgt                                                                1444
```

```
<210> SEQ ID NO 2
<211> LENGTH: 337
<212> TYPE: PRT
<213> ORGANISM: Arabidopsis thaliana
<220> FEATURE:
<221> NAME/KEY: VARIANT
<222> LOCATION: (1)...(337)
<223> OTHER INFORMATION: Xaa=any amino acid

<400> SEQUENCE: 2
```

Met Tyr Ile Lys Glu Leu Thr Glu Thr Asp Glu Glu Lys Arg Glu Arg
1               5                   10                  15

Ser Val Glu Asp Asn Val Asp Asp Gly Asp Lys Ala Val Leu Val Ser
            20                  25                  30

Arg Gly Asn Val Ile Val Ser Thr Thr Lys Arg Ala Leu Val Gly Val
        35                  40                  45

Gly Ala Arg Ala Leu Phe Tyr Pro Thr Leu Val Tyr Asn Val Val Arg
    50                  55                  60

Asn Lys Leu Glu Ser Glu Phe Arg Trp Trp Asp Arg Val Ala Glu Phe
65                  70                  75                  80

Ile Leu Leu Gly Ala Val Pro Phe Pro Ser Asp Val Pro Gln Leu Lys
                85                  90                  95

Xaa Leu Gly Val Cys Gly Val Ile Thr Leu Asn Glu Pro Tyr Glu Thr
              100                 105                 110

Leu Val Pro Ser Ser Leu Tyr Lys Ser Tyr Cys Ile Asp His Leu Val
        115                 120                 125

Ile Ala Thr Arg Asn Tyr Cys Phe Ala Pro Ser Met Glu Ala Ile Cys
    130                 135                 140

Gln Ala Val Glu Phe Ile His Arg Asn Ala Ser Leu Gly Lys Thr Thr
145                 150                 155                 160

Tyr Val His Cys Lys Ala Gly Arg Gly Arg Ser Thr Thr Ile Phe Ile
                165                 170                 175

Cys Tyr Leu Val Gln His Lys Asn Met Thr Pro Glu Ala Ala Tyr Ser
            180                 185                 190

Tyr Val Arg Ser Ile Arg Pro Arg Val Leu Leu Ala Ala Gln Trp
        195                 200                 205

Lys Ala Val Val Glu Tyr Tyr His Val Lys Val Leu Asn Thr Gln Ser
        210                 215                 220

Cys Leu Thr Asp Ala Thr Ser Ala Leu Ile Pro Arg Asn Val Lys Gln
225                 230                 235                 240

Val Cys Ser Gly Asn Val Val Phe Asp Asp Gly Ser Met Val Val
                245                 250                 255

Val Thr His Ser Asp Leu Glu Gly Tyr Asn Asp Asp Ser Arg Ser
            260                 265                 270

Arg Arg Ser Val Lys Val Asn Gly Asn Glu Leu Trp Ala Ala Ala
        275                 280                 285

Asp Leu Ser Met Val Tyr Arg Val Lys Val Gly Gln Ala Ala Met
    290                 295                 300

Ala Arg Ile Ser Cys Leu Trp Leu Gly Leu Arg Glu Asp Gln Lys Leu
305                 310                 315                 320

Ser Gly Lys Asn Leu Ser Met Gly Gly Ile Ser Val Asp Ile Ser Val
                325                 330                 335

Tyr

<210> SEQ ID NO 3
<211> LENGTH: 87
<212> TYPE: PRT
<213> ORGANISM: Arabidopsis thaliana

<400> SEQUENCE: 3

Ile Ala Thr Arg Asp Tyr Cys Phe Ala Pro Ser Met Glu Ala Ile Cys
1               5                   10                  15

Gln Ala Val Glu Phe Ile His Arg Asn Ala Ser Leu Gly Lys Thr Thr
            20                  25                  30

Tyr Val His Cys Lys Ala Gly Arg Gly Arg Ser Thr Thr Ile Val Ile
        35                  40                  45

Cys Tyr Leu Val Gln His Lys Asn Met Thr Pro Glu Ala Ala Tyr Ser
    50                  55                  60

Tyr Val Arg Ser Ile Arg Pro Arg Val Leu Leu Ala Ala Gln Trp
65                  70                  75                  80

Lys Ala Val Val Glu Tyr Tyr
                85

<210> SEQ ID NO 4
<211> LENGTH: 87
<212> TYPE: PRT
<213> ORGANISM: Arabidopsis thaliana

```
<400> SEQUENCE: 4

Val Ile Val Val Asp Lys Glu Asp Thr Asn Leu Glu Met Tyr Phe Asp
 1               5                  10                  15

Glu Cys Val Asp Phe Ile Asp Glu Ala Lys Arg Gln Gly Gly Ser Val
                20                  25                  30

Leu Val His Cys Phe Val Gly Lys Ser Arg Ser Val Thr Ile Val Val
            35                  40                  45

Ala Tyr Leu Met Lys Lys His Gly Met Thr Leu Ala Gln Ala Leu Gln
 50                  55                  60

His Val Lys Ser Lys Arg Pro Val Ala Ser Pro Asn Ala Gly Phe Ile
 65                  70                  75                  80

Arg Gln Leu Gln Asp Leu Glu
                85

<210> SEQ ID NO 5
<211> LENGTH: 87
<212> TYPE: PRT
<213> ORGANISM: Arabidopsis thaliana

<400> SEQUENCE: 5

Ile Pro Thr Arg Asp Tyr Leu Phe Ala Pro Ser Ile Val Asp Ile Thr
 1               5                  10                  15

Leu Ala Val Asn Phe Ile His Lys Asn Ala Leu Leu Gly Lys Thr Thr
                20                  25                  30

Tyr Val His Cys Lys Ala Gly Arg Gly Arg Ser Thr Thr Val Val Leu
            35                  40                  45

Cys Tyr Leu Ile Glu His Lys Ser Met Thr Val Ala Ala Ala Phe Glu
 50                  55                  60

His Val Arg Ser Ile Arg Pro Arg Val Leu Leu His Pro Ser Gln Arg
 65                  70                  75                  80

Lys Val Val Glu Glu Phe Ser
                85

<210> SEQ ID NO 6
<211> LENGTH: 81
<212> TYPE: PRT
<213> ORGANISM: Arabidopsis thaliana

<400> SEQUENCE: 6

Leu Asp Asn Glu Lys Val Leu Gln Phe Asp Asp Ala Ile Lys Phe Leu
 1               5                  10                  15

Asp Gln Cys Glu Lys Asp Lys Ala Arg Val Leu Val His Cys Met Ser
                20                  25                  30

Gly Lys Ser Arg Ser Pro Ala Val Val Val Ala Tyr Leu Met Lys Arg
            35                  40                  45

Lys Gly Trp Arg Leu Ala Glu Ser His Gln Trp Val Lys Gln Arg Arg
 50                  55                  60

Pro Ser Thr Asp Ile Ser Pro Gly Lys Tyr Leu Asp Phe Gly Leu Glu
 65                  70                  75                  80

Thr

<210> SEQ ID NO 7
<211> LENGTH: 87
<212> TYPE: PRT
<213> ORGANISM: Homo sapiens

<400> SEQUENCE: 7
```

```
Ile Pro Val Glu Asp Asn His Lys Ala Asp Ile Ser Ser Trp Phe Asn
 1               5                  10                  15

Glu Ala Ile Asp Phe Ile Asp Ser Ile Lys Asn Ala Gly Gly Arg Val
                20                  25                  30

Phe Val His Cys Gln Ala Gly Ile Ser Arg Ser Ala Thr Ile Cys Leu
            35                  40                  45

Ala Tyr Leu Met Arg Thr Asn Arg Val Lys Leu Asp Glu Ala Phe Glu
        50                  55                  60

Phe Val Lys Gln Arg Arg Ser Ile Ile Ser Pro Asn Phe Ser Phe Met
65                  70                  75                  80

Gly Gln Leu Leu Gln Phe Glu
                85

<210> SEQ ID NO 8
<211> LENGTH: 87
<212> TYPE: PRT
<213> ORGANISM: Homo sapiens

<400> SEQUENCE: 8

Ile Pro Val Glu Asp Asn His Lys Ala Asp Ile Ser Ser Trp Phe Met
 1               5                  10                  15

Glu Ala Ile Glu Tyr Ile Asp Ala Val Lys Asp Cys Arg Gly Arg Val
                20                  25                  30

Leu Val His Cys Gln Ala Gly Ile Ser Arg Ser Ala Thr Ile Cys Leu
            35                  40                  45

Ala Tyr Leu Met Met Lys Lys Arg Val Arg Leu Glu Glu Ala Phe Glu
        50                  55                  60

Phe Val Lys Gln Arg Arg Ser Ile Ile Ser Pro Asn Phe Ser Phe Met
65                  70                  75                  80

Gly Gln Leu Leu Gln Phe Glu
                85

<210> SEQ ID NO 9
<211> LENGTH: 87
<212> TYPE: PRT
<213> ORGANISM: Rat rattus

<400> SEQUENCE: 9

Ile Pro Ile Ser Asp His Trp Ser Gln Asn Leu Ser Gln Phe Phe Pro
 1               5                  10                  15

Glu Ala Ile Ser Phe Ile Asp Glu Ala Arg Gly Lys Asn Cys Gly Val
                20                  25                  30

Leu Val His Cys Leu Ala Gly Ile Ser Arg Ser Val Thr Val Thr Val
            35                  40                  45

Ala Tyr Leu Met Gln Lys Leu Asn Leu Ser Met Asn Asp Ala Tyr Asp
        50                  55                  60

Ile Val Lys Met Lys Lys Ser Asn Ile Ser Pro Asn Phe Asn Phe Met
65                  70                  75                  80

Gly Gln Leu Leu Asp Phe Glu
                85

<210> SEQ ID NO 10
<211> LENGTH: 944
<212> TYPE: DNA
<213> ORGANISM: Mus musculus

<400> SEQUENCE: 10
```

-continued

```
ccatggtgat ggaggtgggc atcctggacg ccggggggct gcgcgcgctg ctgcgagagg    60
gcgccgcgca gtgcctgttg ttggattgtc gctccttctt cgctttcaac gccggccaca   120
tcgcgggctc agtgaacgtg cgcttcagca ccatcgtgcg cgccgcgcc aagggcgcca    180
tgggcctgga gcatatcgtg cccaacgctg aactgcgtgg ccgcctgctg ccggagcct    240
accacgccgt ggtgctgctg gacgagcgca gcgcctccct ggacggcgcc aagcgcgacg   300
gcaccctggc cctggccgcg ggcgcgctct gccgagaggc gcgctccact caagtcttct   360
ttctccaagg aggatatgaa gcgttttcgg cttcctgccc tgagctgtgc agcaaacagt   420
ccaccccccac ggggctcagc ctcccccctga gtactagtgt gcctgacagt gcagaatccg  480
gatgcagctc ctgtagtacc cctctctacg atcaggggg cccagtggag atcctgtcct    540
tcctgtacct gggcagtgcc tatcacgctt ctcggaagga tatgcttgac gccttgggca   600
tcaccgcctt gatcaacgtc tcagccaatt gtcctaacca ctttgagggt cactaccagt   660
acaagagcat ccctgtggag gacaaccaca aggcagacat cagctcctgg ttcaacgagg   720
ctattgactt catagactcc atcaaggatg ctggagggag agtgtttgtt cattgccagg   780
ccggcatctc ccggtcagcc accatctgcc ttgcttacct catgaggact aaccgggtaa   840
agctggacga ggcctttgag tttgtgaagc agaggcggag tatcatctcc ccgaacttca   900
gcttcatggg ccagctgctg cagtttgagt cccaagtgct agcc                    944
```

<210> SEQ ID NO 11
<211> LENGTH: 314
<212> TYPE: PRT
<213> ORGANISM: Mus musculus

<400> SEQUENCE: 11

```
Met Val Met Glu Val Gly Ile Leu Asp Ala Gly Gly Leu Arg Ala Leu
 1               5                  10                  15

Leu Arg Glu Gly Ala Ala Gln Cys Leu Leu Asp Cys Arg Ser Phe
                20                  25                  30

Phe Ala Phe Asn Ala Gly His Ile Ala Gly Ser Val Asn Val Arg Phe
            35                  40                  45

Ser Thr Ile Val Arg Arg Ala Lys Gly Ala Met Gly Leu Glu His
         50                  55                  60

Ile Val Pro Asn Ala Glu Leu Arg Gly Arg Leu Leu Ala Gly Ala Tyr
 65                  70                  75                  80

His Ala Val Val Leu Leu Asp Glu Arg Ser Ala Ser Leu Asp Gly Ala
                85                  90                  95

Lys Arg Asp Gly Thr Leu Ala Leu Ala Ala Gly Ala Leu Cys Arg Glu
            100                 105                 110

Ala Arg Ser Thr Gln Val Phe Phe Leu Gln Gly Gly Tyr Glu Ala Phe
        115                 120                 125

Ser Ala Ser Cys Pro Glu Leu Cys Ser Lys Gln Ser Thr Pro Thr Gly
    130                 135                 140

Leu Ser Leu Pro Leu Ser Thr Ser Val Pro Asp Ser Ala Glu Ser Gly
145                 150                 155                 160

Cys Ser Ser Cys Ser Thr Pro Leu Tyr Asp Gln Gly Gly Pro Val Glu
                165                 170                 175

Ile Leu Ser Phe Leu Tyr Leu Gly Ser Ala Tyr His Ala Ser Arg Lys
            180                 185                 190

Asp Met Leu Asp Ala Leu Gly Ile Thr Ala Leu Ile Asn Val Ser Ala
        195                 200                 205
```

```
-continued

Asn Cys Pro Asn His Phe Glu Gly His Tyr Gln Tyr Lys Ser Ile Pro
    210             215                 220

Val Glu Asp Asn His Lys Ala Asp Ile Ser Ser Trp Phe Asn Glu Ala
225             230                 235                 240

Ile Asp Phe Ile Asp Ser Ile Lys Asp Ala Gly Gly Arg Val Phe Val
                245                 250                 255

His Cys Gln Ala Gly Ile Ser Arg Ser Ala Thr Ile Cys Leu Ala Tyr
            260                 265                 270

Leu Met Arg Thr Asn Arg Val Lys Leu Asp Glu Ala Phe Glu Phe Val
            275                 280                 285

Lys Gln Arg Arg Ser Ile Ile Ser Pro Asn Phe Ser Phe Met Gly Gln
    290                 295                 300

Leu Leu Gln Phe Glu Ser Gln Val Leu Ala
305                 310
```